United States Patent [19]
Jandak et al.

[11] Patent Number: 6,123,084
[45] Date of Patent: Sep. 26, 2000

[54] METHOD FOR IMPROVING BLOOD FLOW IN THE HEART

[75] Inventors: Jennifer Jandak, Palo Alto; Michael J. Rosinko; Michael Horzewski, both of San Jose; Alexander Khairkhahan, Palo Alto, all of Calif.

[73] Assignee: Eclipse Surgical Technologies, Inc., Sunnyvale, Calif.

[21] Appl. No.: 09/216,283

[22] Filed: Dec. 18, 1998

[51] Int. Cl.$^7$ ................................................ A61B 19/00
[52] U.S. Cl. ......................... 128/898; 606/27; 606/167; 604/22; 607/122
[58] Field of Search ................................... 128/898, 897; 606/27, 29, 46, 167; 600/10; 604/22; 607/122

[56] References Cited

U.S. PATENT DOCUMENTS

| | | |
|---|---|---|
| 4,869,248 | 9/1989 | Narula . |
| 4,947,842 | 8/1990 | Marchosky et al. . |
| 5,103,804 | 4/1992 | Abele et al. . |

FOREIGN PATENT DOCUMENTS

WO96/35469  4/1996  WIPO .

*Primary Examiner*—Michael J. Milano
*Assistant Examiner*—Dinh X. Nguyen
*Attorney, Agent, or Firm*—Paul Davis; Ilene Lapidus Janofsky; Ross M. Carothers

[57] ABSTRACT

A method for improving blood flow in the heart provides a catheter system with an outer catheter defining at least one lumen and an inner catheter defining at least one lumen with proximal and distal portions. An introducer is coupled to the distal portion of the inner catheter. The introducer has a tissue piercing distal end. A resistive heater element is positioned in the introducer. The catheter system is introduced into a patient's vasculature. The inner catheter is then introduced through the a lumen of the outer catheter to a selected heart site. The tissue piercing distal end of the introducer is then advanced into an interior of the heart at the selected heart site. Energy is delivered to the selected heart site from the resistive heater element to create a blood conducting pathway and/or stimulate angiogenesis. In an alternative embodiment, a heart treatment apparatus is provided that includes a handpiece with a proximal and a distal end and an elongated member defining at least one lumen coupled to the handpiece distal end. The elongated member has a distal end and an introducer coupled to the distal end. The introducer has a tissue piercing distal end. A resistive heater element is positioned in the introducer. The tissue piercing distal end is introduced through a port in the chest wall into a chest cavity and through an epicardial surface of the heart wall to a selected site within the heart. Energy is delivered to the selected heart site from the resistive heater element to create a blood conducting pathway and/or stimulate angiogenesis.

64 Claims, 13 Drawing Sheets

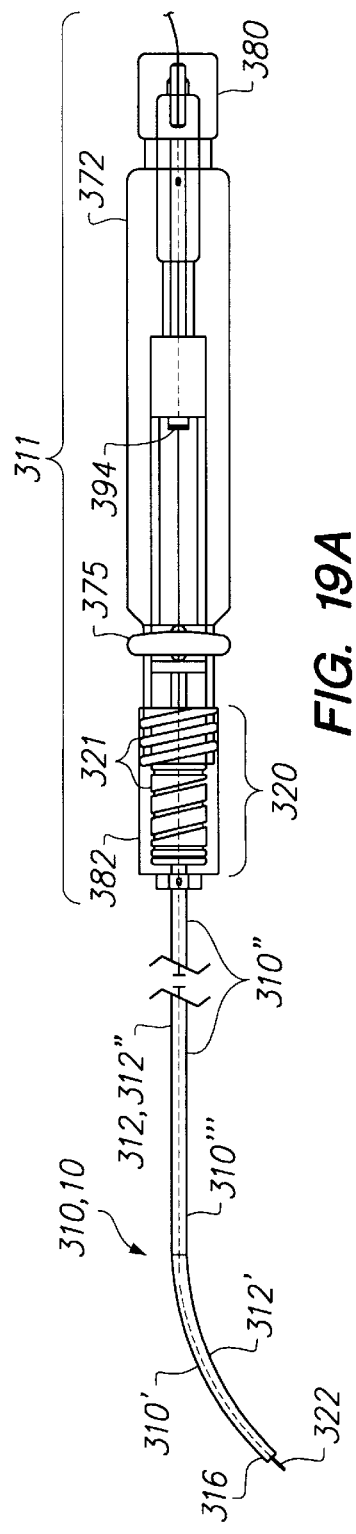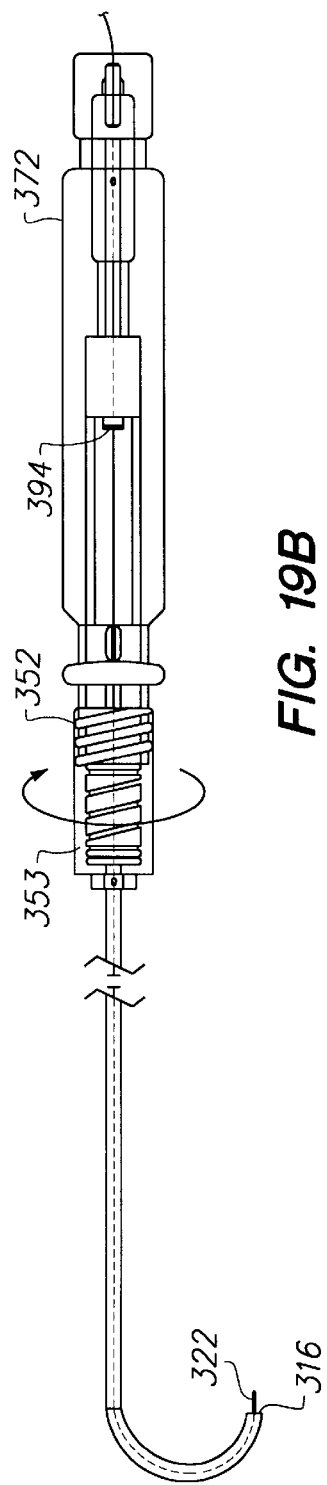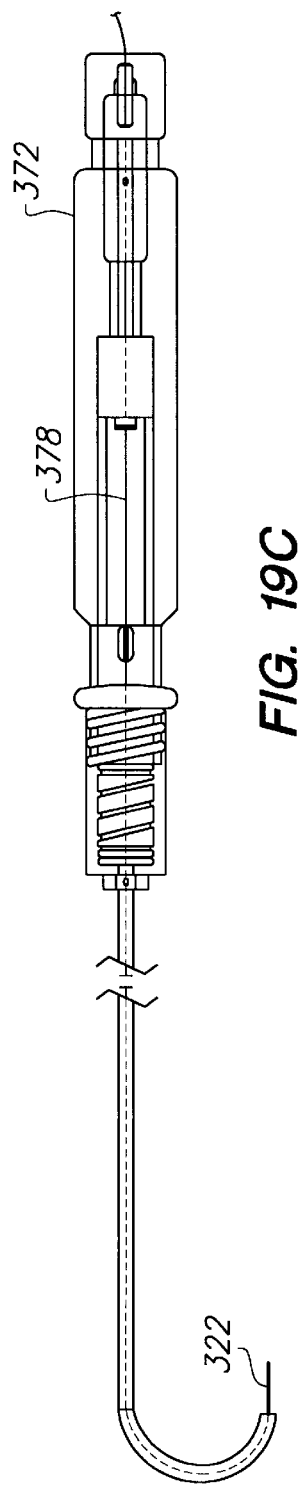

METHOD FOR IMPROVING BLOOD FLOW IN THE HEART

BACKGROUND OF THE INVENTION

1. Field of the Invention

This invention relates to a method for improving blood flow in the heart, and more particularly to a method for performing transmyocardial revascularization or stimulating angiogenesis using a resistive heater.

2. Description of Related Art

Heart disease is a common medical problem in developed countries. The major cause of heart disease in developed countries is impaired blood flow to the heart. The coronary arteries which supply blood to the heart become narrowed due to a disease known as atherosclerosis and as a result, part of the heart muscle is deprived of oxygen and other nutrients. The resulting condition known as ischemia can lead to angina pectoris, a pain in the chest, arms or jaw due to a lack of oxygen to the heart, or the infarction or death of an area of the myocardium caused by the ischemia.

Techniques to supplement the flow of oxygenated blood directly from the left ventricle into the myocardial tissue have included needle acupuncture to create transmural channels, implantation of T-shaped tubes into the myocardium and the like. Efforts to graft the omentum, parietal pericardium, or mediastinal fat to the surface of the heart have had limited success. Others have attempted to restore arterial flow by implanting the left internal mammary artery into the myocardium.

Coronary artery blockage can be treated with a variety of different modalities. Drug therapy is used to dilate the arteries and dissolve clots. Examples of medicaments used in dilation include nitrates, beta-blockers and peripheral vasodilatator drugs. Transluminal angioplasty is performed by inflating a balloon at a narrowed or clogged site in the artery. When drug therapy is ineffective or angioplasty is too risky, coronary artery bypass grafting (CABG) may be performed. CABG is a major surgical procedure requiring opening the chest and the use of a heart-lung machine.

Another method of improving myocardial blood supply is transmyocardial revascularization (TMR) where channels are formed from the epicardial to the endocardial portions of the heart. TMR relieves ischemia by allowing blood to pass from the ventricle through the channels either directly into other vessels perforated by the channels or into myocardial sinusoids which connect to the myocardial microcirculation. By analogy, TMR has been compared to transforming the human heart into one functionally resembling that of a reptile with respect to myocardial blood flow.

In the reptilian heart, blood flow occurs via communicating channels between the left ventricle and the coronary arteries (Frazier, O. H.: Myocardial Revascularization with Laser—Preliminary Findings, Circulation, 1995; 92 [suppl II]:II-58–II-65). There is evidence of these communicating channels in the developing human embryo. In the human heart, myocardial microanatomy includes the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR methods using lasers to create channels in the myocardium. These studies have demonstrated histological evidence of probable new vessel formation (a process known as angiogenesis) adjacent to collagen occluded transmyocardial channels. In contrast, studies of myocardial acupuncture or boring, (mechanically displaces or removes tissue), showed acute thrombosis followed by organization and fibrosis of clots as the principal mechanism of channel closure.

U.S. Pat. No. 4,658,817 discloses a method and apparatus for TMR using a laser. A surgical $CO_2$ laser includes a handpiece for directing a laser beam to a desired location. Mounted on a forward end of the handpiece is a hollow needle to be used in surgical applications where the needle perforates a portion of tissue to provide the laser beam direct access to distal tissue.

U.S. Pat. No. 5,125,926 (the "'926 Patent") teaches a heart-synchronized pulsed laser system for TMR. In the '926 Patent, contraction and expansion of a beating heart are monitored. During monitoring, the apparatus triggers the delivery of a pulse of laser energy to the heart during a predetermined portion of the heartbeat cycle. This heart-synchronized pulsed laser system is important where the energy and pulse rate of the particular type of laser are potentially damaging to the beating heart or it's action. Application of laser energy to a beating heart can induce fibrillation or arrhythmia. Additionally, as the heart beats, the spatial relationship between the heart and the tip of the laser delivery probe may change so that the necessary power of the beam and the required position of the handpiece may be unpredictable.

U.S. Pat. No. 5,380,316 (the "'316 Patent") and U.S. Pat. No. 5,389,096 (the "'096 Patent) both disclose respectively, systems and methods for intra-operative and percutaneous myocardial revascularization. The '316 Patent is related to TMR performed by inserting a portion of an elongated flexible lasing apparatus into the chest cavity of a patient and lasing channels directly through the outer surface of the epicardium into the myocardium tissue. In the '096 Patent, TMR is performed by guiding an elongated flexible lasing apparatus into a patient's vasculature such that the firing end of the apparatus is adjacent to the endocardium. Channels are created directly through the endocardium into the myocardium tissue without perforating the pericardium layer.

The use of lasers as the energy source in TMR has deficiencies. Lasers can be very expensive energy sources. Also, those lasers which permit acceptable depths of tissue necrosis provide a low volumetric ablation rate.

RF energy has also been disclosed as an alternative energy source for TMR as described in U.S. Pat. No. 5,683,366 (the "'366 Patent"). In the '366 Patent, a probe is introduced into a thoracic cavity of a patient through a percutaneous penetration, a thoracotomy or a sternotomy. An RF electrode is positioned adjacent to a wall of the patient's heart. An electrically conducting liquid is directed to the heart wall to provide a current flow path. High frequency voltage is applied to ablate or otherwise disintegrate tissue at the heart wall. The probe is then axially translated towards the ventricular wall to form a revascularizing channel or artificial vessel from the ventricle to the myocardium in order to increase blood flow.

One drawback of many RF devices used for tissue ablation is an inability to control the depth of necrosis (e.g. cell death) in the tissue being treated. Most electrosurgical devices rely on the creation of an electric arc between the treating electrode and the tissue being cut or ablated to cause the desired localized heating. Such arcs, however, often create very high temperatures causing a depth of tissue necrosis greater than 500 $\mu$m, frequently greater than 800

μm, and sometimes as great as 1700 μm. The inability to control such depth of tissue necrosis is a significant disadvantage in the use of RF energy for TMR applications.

PTC Application WO 96/35469 discloses the use of lasers, a rotating auger device, a circular cutting device, a high velocity fluid jet and resistive heating device as channel forming devices. The limitations of lasers are discussed herein. The cutting and fluid devices present the risk of coronary and cerebral embolisms from small pieces of dislodged tissue causing emboli that lodge in a coronary or cerebral artery. While disclosed embodiments of the resistive heating device have the limitation of not being able to precisely control the depth of penetration into coronary tissue.

There is a need for a TMR method and apparatus which uses a relatively simple energy source. There is a further need for a TMR energy source which provides both localized and controllable heating. Yet there is a further need for a method and apparatus which use resistive heating to create revascularization channels and/or stimulate angiogenesis. Still a further need exists for a method and apparatus using resistive heating to create revascularization channels and/or stimulate angiogenesis by piercing a heart wall prior to the delivery of thermal energy from the resistive heating source. Still yet another need exists for a method and apparatus using resistive heating to create revascularization channels and/or stimulate angiogenesis by heating the resistive heating source prior to piercing a heart wall.

SUMMARY OF THE INVENTION

Accordingly, an object of the invention is to provide a method for improving blood flow in the heart.

Another object of the invention is to provide a method for improving blood flow in the heart by the creation of blood conducting pathways.

Yet another object of the invention is to provide a method for improving blood flow in the heart by the creation of revascularization channels.

Still another object of the invention is to provide a method for improving blood flow in the heart by stimulating angiogenesis.

Yet another object of the invention is to provide a resistive heating source to create revascularization channels and/or stimulate angiogenesis.

Another object of the invention is to provide a resistive heating source in a catheter or catheter system with a piercing distal end that delivers thermal energy to a selected heart site after the resistive heating source has been introduced into the heart wall.

Still yet another object of the invention is to provide a resistive heating source in a catheter or catheter system with a piercing distal end that delivers thermal energy to a selected heart site where the resistive heating source is heated prior to being introduced into the heart wall.

These and other objects of the invention are achieved in a method for improving blood circulation to the heart that provides a catheter system that includes an outer catheter with an outer catheter distal end and at least one outer catheter lumen and an inner catheter configured to be advancable in the outer catheter. The inner catheter has a proximal portion, a distal portion, at least one inner catheter lumen, an introducer with a tissue piercing distal end coupled to the distal portion and a resistive heater element positioned in the introducer. The catheter system is introduced through a vasculature and the inner catheter body is advanced through the outer catheter body into the heart. The tissue piercing distal end of the introducer is introduced into the heart. Energy is controllably delivered from the resistive heater element to a selected heart tissue site to create a blood conducting pathway in the patient's heart including a revascularization channel.

In still yet another embodiment, a method of improving blood circulation in a patient's heart provides a heart treatment apparatus that includes a handpiece with a proximal and a distal end and an elongated member coupled to the handpiece distal end. The elongated member has a proximal portion and a distal portion and defines at least one lumen. The elongated member distal portion is coupled to an introducer with a tissue piercing distal end and a resistive heater element is positioned in the introducer. The tissue piercing distal end is advanced through an epicardial surface and into an interior of the heart. Energy is controllably delivered from the resistive heater element to a selected heart tissue site to create a blood conducting pathway in the patient's heart including a revascularization channel.

In still a further embodiment, a method of improving blood circulation in a patient's heart provides a heart treatment system that includes a handpiece with a proximal end and a distal end and an inner elongated catheter that is positionable within an outer elongated member. The outer elongated member has an outer elongated member proximal portion, an outer elongated member distal portion and defines at least one outer elongated member lumen. The outer elongated member proximal portion is coupled to the handpiece distal end. The inner catheter includes a proximal portion and a distal portion and defines at least one inner catheter lumen. The inner catheter distal portion is coupled to an introducer with a tissue piercing distal end and a resistive heater element is positioned in the introducer. The tissue piercing distal end is advanced through an epicardial surface and into an interior of the heart. Energy is controllably delivered from the resistive heater element to a selected heart tissue site to create a blood conducting pathway in the patient's heart including a revascularization channel.

BRIEF DESCRIPTION OF THE FIGURES

FIGS. 19A, 19B and 19C are lateral views of an embodiment of the catheter system with a tip alignment mechanism illustrating the function of the mechanism.

DETAILED DESCRIPTION OF THE PREFERRED EMBODIMENTS

In various embodiments, the present invention provides means for creating or otherwise stimulating the genesis of blood conducting pathways in myocardial tissue so as to allow oxygenated blood to perfuse from the ventricle into the wall of the heart muscle including the interior or endocardium layer, the middle or myocardium layer and the outer or epicardial layer. The pathways include channels, pockets or zones in the heart wall which directly or indirectly serve to increase blood flow to portions of the heart muscle that are ischemic or otherwise deprived of adequate blood supply due to the construction of one or more supplying coronary arteries. These arteries become constricted by fibrous and/or calcified plaques caused by atherosclerosis and related cardiovascular diseases. By reestablishing blood supply to the ischemic sections of the heart (a process known as revascularization), the pathways improve the pumping function of the heart muscle and reduce a condition known as an angina, or chest pain caused by insufficient blood supply to the heart.

In various embodiments of the invention, sufficient energy is delivered to one or more selected sites in the heart wall (including endocardial, myocardial or epicardial sites) to stimulate angiogenesis (e.g. the creation of new blood vessels). In one embodiment, angiogenesis is produced by delivering thermal energy to a selected site sufficient to induce a wound healing response. The tissue morphology in the area of the wound healing response includes a wound space adjacent a gradient zone of local ischemia which is populated by dividing fibroblasts. Behind the leading zone is an area of active collagen synthesis characterized by mature fibroblasts, new tissue growth, and numerous newly-formed capillaries.

Various embodiments of the present invention for creating blood conducting pathways and/or improving blood flow or circulation to the heart can include both percutaneous and surgical embodiments. Surgical embodiments allow the physician to access the intended treatment site in the heart during an open chest procedure in which the heart is exposed directly or via surgical access ports discussed herein. Percutaneous embodiments allow the physician to access the heart wall by a catheter device percutaneously introduced into an artery or vein and then advanced through arterial or venous system into the ventricle of the heart.

Figure 1:
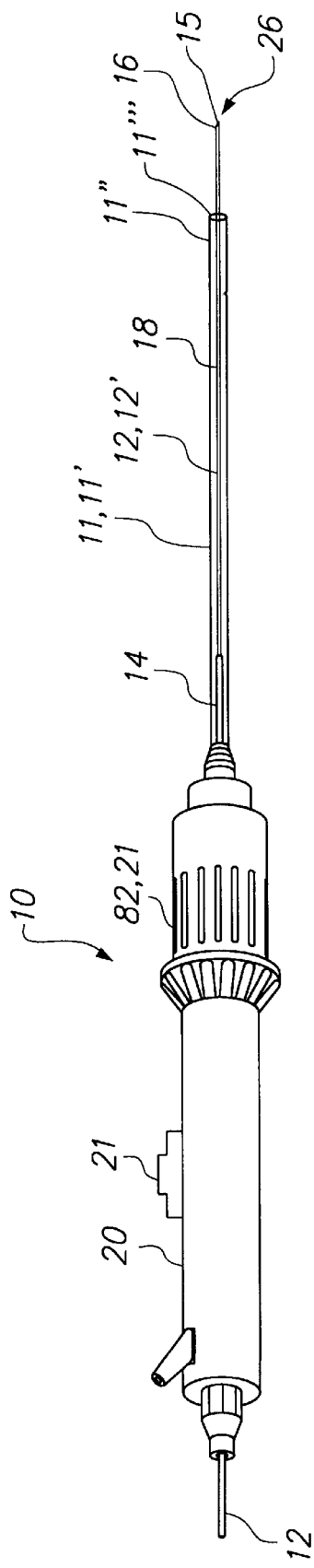
FIG. 1 is a representative isometric view of the catheter system of the present invention showing a handpiece with a deflection component.

Referring now to FIG. 1, one embodiment of the invention includes a revascularization system 10, also called a catheter system 10 comprising an outer catheter 11 (which can also be an outer jacket discussed herein) with an outer elongated catheter body 11', a distal portion 11" and at least one outer catheter lumen 11'" (also called lumens 11'") disposed within outer catheter 11 and an inner catheter 12 positionable within outer catheter 11. Inner catheter 12 includes an elongated inner catheter body 12', a proximal portion 14, a distal portion 16, one or more inner catheter lumens 15 (also called lumens 15) disposed within the inner catheter body 12'. Outer catheter 11 and outer catheter lumen 11'" are configured to allow axial advancement of inner catheter 12 through outer catheter lumen 11'". Inner catheter 12 is further configured to be advanceable within the lumen 11'" of the outer catheter body 11', such that the distal portion 16 of inner catheter 12 can be maneuvered from a percutaneous vascular entry point, through the vasculature to a variety of sites in the arterial and venous systems including various positions within the atrial and ventricular chambers of the heart, including the endocardial, myocardial and epicardial layers of the heart wall.

In various embodiments, inner catheter proximal portion 14 can be coupled to a handpiece 20 (by a Toughy-Borst or other catheter connector known in the art, not shown) which can be used to laterally bend and/or advance inner catheter 12 in an axial direction. In alternative embodiments, the proximal portion of outer catheter 11 can be coupled to handpiece 20 (by a connector described above), with inner catheter 12 moving freely inside outer catheter 11.

The distal portion 16 of inner catheter 12 is more flexible than central torquing portion 18, to allow distal portion 16 to develop a controlled bend with a smaller radius of curvature. Inner catheter body 12' can be made of a braided or "laid-up" type of construction. The braided construction enhances resistance to sidewall collapse, facilitates torque transmission and twisting without catheter whip, and provides enhanced columnar support during catheter deflection. In various embodiments, inner catheter 12 can be flexible or rigid. The rigidity of inner catheter 12 can be configured for and/or relative to the sharpness of the introducer tip at distal end 26. In one embodiment, the rigidity of inner catheter 12 can be selectable and/or controlled through the use of a column strength member described herein. A deflection device 21 is coupled to handpiece 20 and is activateable by the user to deflect inner catheter distal portion 16 a selectable amount which, in various embodiments, can be in the range from 0 to 360°, with a preferred range of 0 to 180°. Deflection device 21 comprises a deflection knob, pull wire, pull cable stop and deflection housing tube all described herein.

Figure 2B:
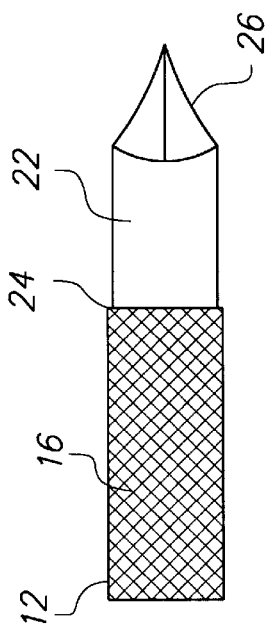
FIG. 2B is a close-up perspective view of the distal portion of the inner catheter illustrated in FIG. 1 illustrating a tissue piercing introducer coupled to a distal portion of the inner catheter, where the tissue piercing distal end of the introducer is a trocar point.
Figure 2A:
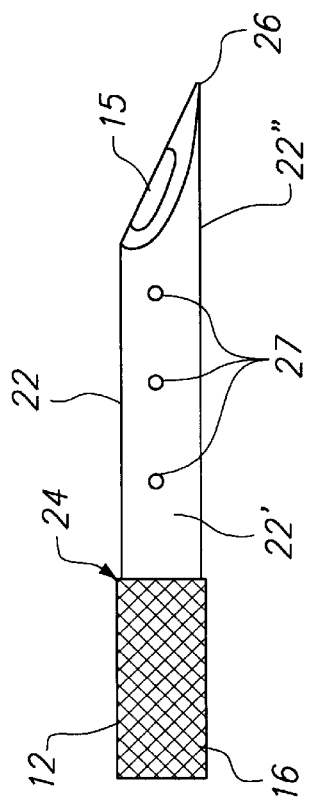
FIG. 2A is a close-up perspective view of the distal portion of an inner catheter illustrated in FIG. 1 illustrating a tissue piercing introducer coupled to a distal portion of the inner catheter, where the tissue piercing distal end of the introducer is a hypodermic needle.

As illustrated in FIG. 2A, an introducer 22 is coupled to the distal portion 16 of inner catheter 12. Introducer 22 can be coupled to the distal portion 16 of catheter 12 with a coupling member 24 that reduces kinking. Suitable coupling methods include adhesive bonding, hot melt and crimping techniques all well known in the art. Introducer 22 has a tissue piercing distal end 26 which is sufficiently sharp to pierce an endocardium wall of a patient's heart for insertion into an interior section of the heart wall, preferably the myocardium. Introducer 22 is made of a material with sufficient rigidity to be advanceable through the endocardium by the application of longitudinal force or torque from inner catheter body 12' and/or handpiece 20. Introducer 22 can be made of a variety of materials including, but not limited to, metal, braided polymer tubing, polyimide, ceramic and other medical materials known in the art. In one embodiment shown in FIG. 2A, introducer 22 is a hypodermic needle having a beveled tip. In another embodiment shown in FIG. 2B, introducer 22 is a trocar and may include a three-sided trocar point. In one or more embodiments, introducer 22 is constructed to be less flexible (e.g. has a higher bending stiffness) than inner catheter body 12'. Introducer 22 is coupled to distal portion 16 of inner catheter body 12' with a coupling member 24. Coupling member 24 can be a metal or plastic band made using materials well known in the art such as stainless steel or PET heat-shrink tubing. Also coupling member 24 can be attached to introducer 22 and inner catheter body 12' using adhesive bonding (e.g. using medical grade epoxy or UV adhesives), a hot melt junction, crimping, solvent bonding and other joining techniques well known in the art. A distal end 26 of introducer 22 is tissue piercing. In various embodiments (not shown), introducer 22 can have thermally conductive and nonconductive regions.

Figure 3:
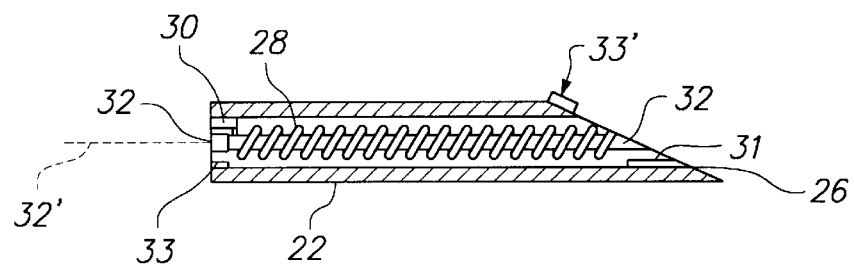
FIG. 3 is a sectional view of the introducer illustrated in FIGS. 2A and 2B.
Figure 4:
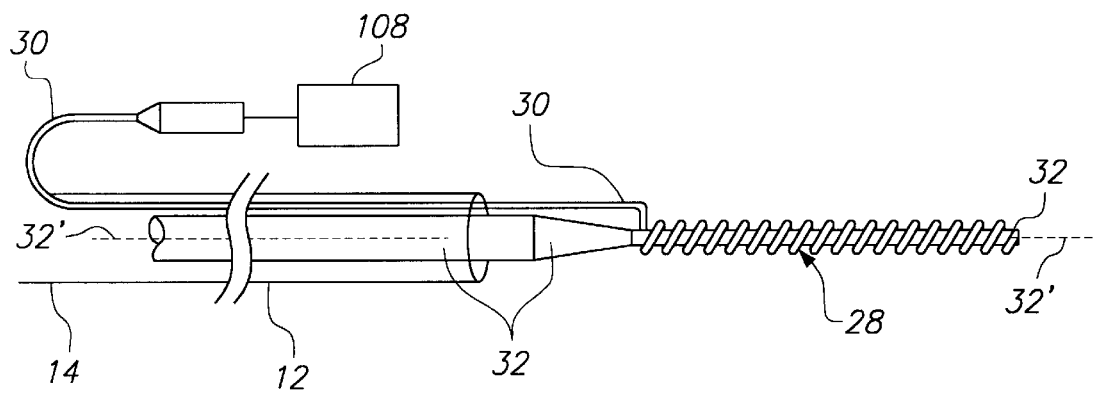
FIG. 4 illustrates the relationship of the resistive heater element of FIGS. 2A and 2B with a column strength member that is at least partially positioned in the introducer.

Referring now to FIGS. 3 and 4, an energy delivery device 28 is positioned in an interior of introducer 22 and preferably extends from the distal portion 16 of inner catheter body 12'. Energy delivery device 28 is coupled to an energy or power source 108. In various embodiments, energy delivery device 28 is affixed in an interior of introducer 22 using adhesive (such as epoxy) or other bonding methods known in the art. Suitable energy delivery devices 28 and energy sources that may be employed in one or more embodiments of the invention include, but are not limited to, the following: (i) a radio-frequency (RF) electrode coupled to an RF source, (ii) a resistive heating element coupled to an electrical power source, (iii) an optical fiber coupled to a coherent or incoherent source of light, (iv) a thermally conductive element thermally coupled to a heated fluid (which may be coupled to a heated fluid source) coupled to a catheter with a lumen configured to receive the heated fluid, (v) a microwave antenna coupled to a microwave source providing energy from 915 MHz to 2.45 GHz, (vi) an ultrasound emitter coupled to an ultrasound power source, wherein the ultrasound power source produces energy in the range of 300 KHZ to 3 GHz, or (vii) a thermally conductive frictional stationary element frictionally coupled to a moving element.

For ease of discussion for the remainder of this application, energy delivery device 28 is a resistive heating element and the power source 108 is an electrical power source well known in the art. However, all of the other herein mentioned energy delivery devices and power sources are equally applicable to catheter system 10.

Resistive heater element 28 can have a length in the range of 2 to 10 mm, with a preferred range of 4 to 10 mm and specific embodiments of 4, 6 and 8 mms. A portion of resistive heater element 28 can extend proximally into distal portion 16 of inner catheter body 12'. In one embodiment, resistive heater element 28 extends within the distal portion 16 of inner catheter body 12', but does not extend as far as the position of coupling member 24 in order to reduce kinking. Resistive heater element 28 can be epoxied to distal end 26 of introducer 22 and coupled to a conductive wire 30. Conductive wire 30 is made of any suitable electrical conductive material (e.g. copper or copper clad stainless steel). In various embodiments, wire 30 extends proximally within lumen 15 in inner catheter body 12'. All of conductive wire 30 is electrically insulated. Conductive wire 30 delivers electrical energy from a resistive heating energy source (not shown) to resistive heater element 28. Conductive wire 30 can be welded to resistive heater element 28 by methods well known to those skilled in the art. In an alternative embodiment (not shown), the distal end 26 of introducer 22 may be heated by laser energy delivered to distal end 26 by a bundle of optical fibers disposed within inner catheter body 12' (or outer catheter body 11') and optically coupled to a laser energy source. Also, introducer 22 may itself comprise a bundle of optical fibers optically coupled to a laser light source.

As shown in FIGS. 3 and 4, in various embodiments a column strength member 32 can extend from the proximal portion 14 of inner catheter body 12' through a portion or all of the length of introducer 22. In other embodiments, member 32 may proximally extend through the entire length of catheter 12 or only a portion. Column strength member 32 adds column strength to introducer 22 to assist its introduction through heart tissue and is preferably made of stainless steel or other metals and rigid plastics known in the art. In one embodiment where column strength member 32 is only positioned in introducer 22, the bending stiffness of column strength member 32, and hence introducer 22, is greater than inner catheter body 12'. In various embodiments, column strength member 32 can extend proximally to handpiece 20 and can be integral to or otherwise disposed within inner catheter 12. In related embodiments, column strength member 32 can function as conductive wire 30 or other electrical lead (not shown) and be coupled to energy delivery device 28 and/or power source 108. In these embodiments, column strength member 32 can be constructed from copper clad stainless steel and may be insulated.

The stiffness of column strength member 32 can vary along its longitudinal axis 32'. In various embodiments, the stiffness can either increase or decrease going from the proximal to the distal direction. Stiffness increases can be achieved through a variety of means including increases in the diameter of member 32 which can occur in a step fashion or in a linear, S-curve, logarithmic or other mathematical manner known in the art. In various other embodiments, changes in the stiffness of column strength member 32 can also be achieved through the use of phase transition metals that undergo changes in their elasticity (and hence stiffness) with changes in temperature. One such group of materials are nickel titanium alloys known as nitinol, whose use in vascular medical products is well known in the art. Upon heating above a fixed temperature (known in the art as the austenite temperature), the elasticity of nitinol significantly increases. The alloy of nitinol used can be engineered to have an austenite temperature within a selected range which can in the area of body temperature (e.g. 37° C.) or higher, such as in the range of 40 to 65° C., with specific embodiments of 45, 50, 55 and 60° C. Thus, the stiffness of column strength member 32 can be controllable in vivo by a change in the temperature of member 32. Specifically, the stiffness of member 32 can be reduced (e.g. flexibility increased) by heating member 32 directly or indirectly using resistive heating element 28 (to a austenite temperature described herein) or via heat transferred from tissue and flowing blood. Likewise, the stiffness of member 32 can increased by cooling member 32 below a temperature described herein.

In various embodiments, the diameter of column strength member 32 can be in the range from 0.004 to 0.020" with specific embodiments of 0.012, 0.014, 0.016 and 0.018". The cross-sectional diameter of column strength member 32 can be larger in inner catheter body 12' than its cross-sectional diameter in introducer 22. Column strength member 32 can be centrally positioned in introducer 22. Resistive heater element 28 may be positioned in a surrounding relationship to column strength member 32. A radio-opaque marker 31 can be positioned on introducer 22 for visualization purposes. A thermal sensor 33, which can be a thermocouple or thermistor, is coupled to introducer 22. A tissue contact sensor 33' may also be coupled to introducer 22 for detecting contact of introducer 22 including distal end 26 with endocardial, myocardial and epicardial tissue. Possible sensors to be used for contact sensor 33' include, but are not limited to, strain gauges, LVDTs, impedance, capacitance and optical sensors known in the art. Additionally, sensor 33' can be used to determine the amount of longitudinal (e.g. axial) advancement of introducer 22.

Figure 5A:
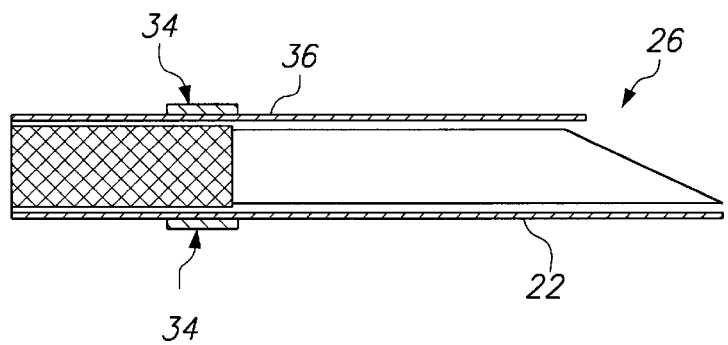
FIG. 5A is a perspective view of the distal portion of the catheter system with the introducer and the inclusion of a stop band and a sleeve or coating that protects the outer catheter from penetration by the needle during needle advancement.
Figure 5B:
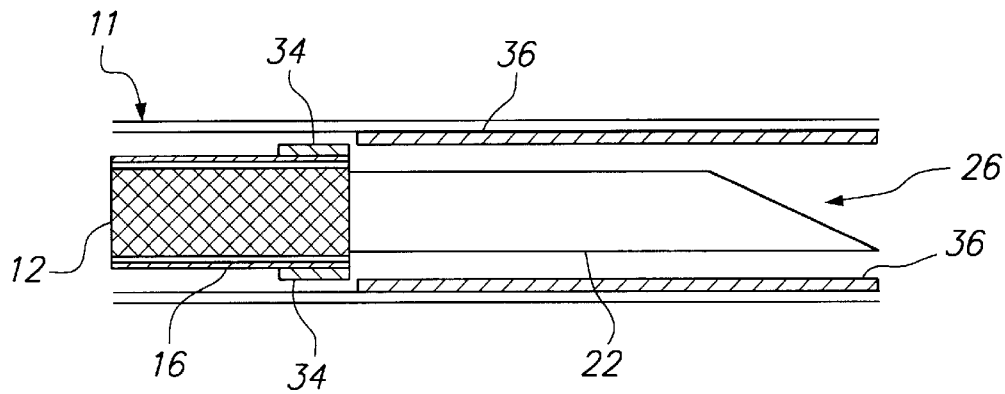
FIG. 5B is a perspective view of the distal portion of the catheter system illustrating the use of a sheath or coating to protect the interior of the distal end of the outer catheter during advancement of the needle through the vasculature.

The advancement of introducer 22 into heart tissue is controlled. In one embodiment illustrated in FIGS. 5A and 5B, such control can be achieved through the use of a stop band 34 positioned at about the juncture of introducer 22 with distal portion 16 of inner catheter body 12'. Also shown in FIG. 5A, an external layer or sheath 36 (which can also be a sheath layer 36 or coating 36) made of material which reduces tissue adherence can be positioned on or applied to the exterior of introducer 22 as well as a portion of inner catheter body 12'. Suitable materials for coating 36 include Teflon® coating which serves to reduces tissue adherence but will not affect the advancement of introducer 22. FIG. 5B shows sheath layer or coating 36 positioned on or in distal portion 11" of outer catheter 11 to protect outer catheter 11, including outer catheter distal portion 11", from puncture by introducer 22 (including distal end 26) during axial advancement of inner catheter 12 through outer catheter 11. In these and related embodiments, sheath layer 36 can be made from a puncture resistant material such as polyimide, nylon, polyolefin (e.g. polyethylene or polyester etc.) or metal.

Figure 6:
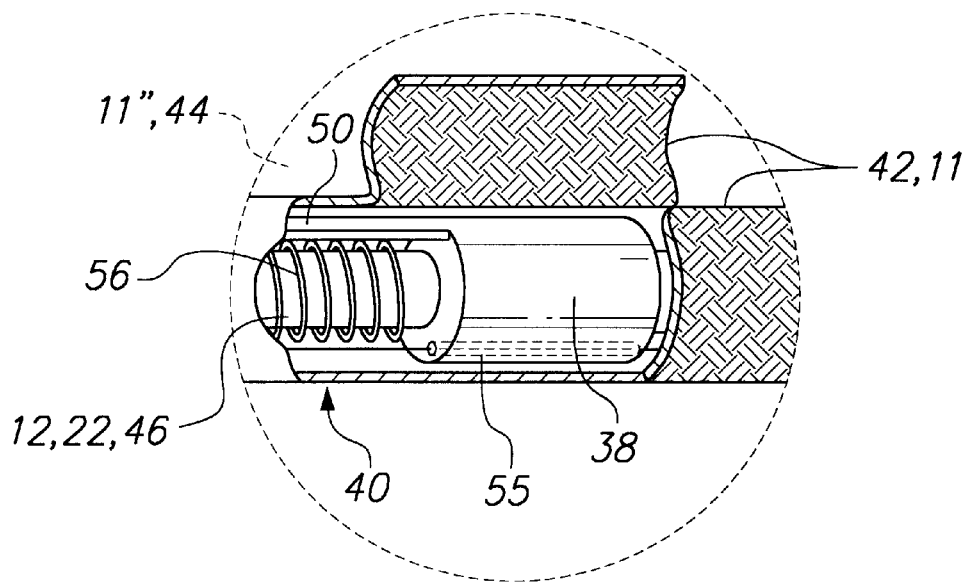
FIG. 6 is a representative isometric view of the inner catheter showing a shim anchor sleeve keyed to the inside of an outer catheter or jacket and located adjacent to a junction between different types of outer jacket constructions.
Figure 7:
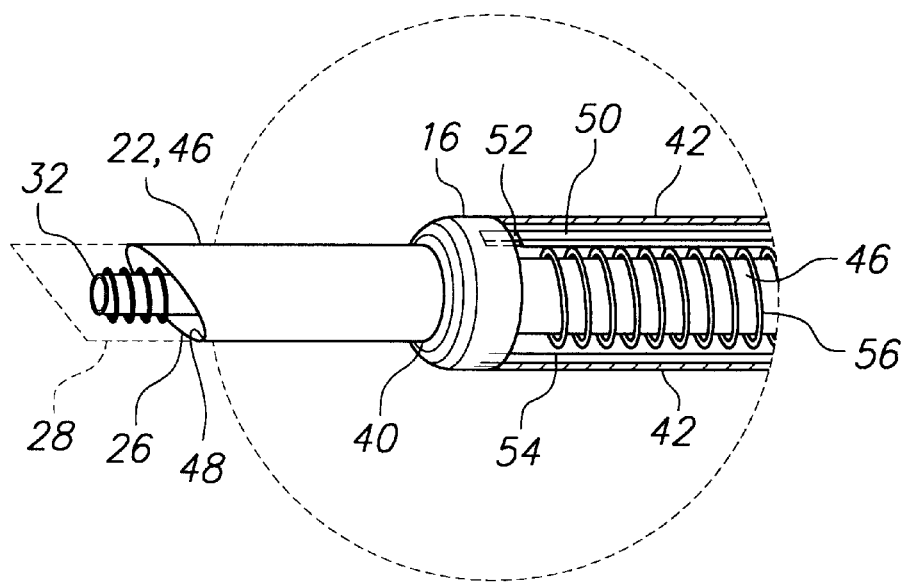
FIG. 7 is a representative cutaway isometric view illustrating one embodiment of the distal portion of the catheter system shown in FIG. 1.

In one embodiment illustrated in FIGS. 6 and 7, inner catheter 12 includes a shim anchor sleeve 38 adjacent to a junction 40 of distal portion 16 and central torquing portion 18 of inner catheter body 12'. A proximal outer jacket portion 42 (which can be part of outer catheter 11) extends from handpiece 20 to junction 40. A distal outer jacket portion 44 (which can also be part of outer catheter 11) extends from the junction 40 to distal portion 16 of inner catheter body 12'.

A center tube 46 (which can also be inner catheter 12) extends at least partially through outer catheter body 11' (and/or inner catheter body 12') and is attached at one end to distal portion 16. A proximal end of center tube 46 is free and floats within handpiece 20, thereby allowing center tube 46 to slide and move during deflection of inner catheter distal portion 16 or outer catheter distal portion 11". Center tube 46 defines a hollow, central passageway 48 through center tube 46 for insertion of an energy delivery device 28, such as a resistive heating element. Center tube 46 can be made of a variety of materials including, but not limited to, polypropylene or other polymeric material that resists collapse by external forces and also during bending and twisting of inner catheter body 12'. Center tube 46 can also act as a "hypo" tube known in the art. An additional tube inside center tube 46, or annularly inside or outside center tube 46, can be provided for delivery of fluids, working tools and the like.

Center tube 46 slidably extends through shim anchor sleeve 38 which is attached to the inner wall of outer jacket portion 42. Shim anchor sleeve 38 is coupled to the distal portion 16 of inner catheter body 12'. Shim anchor sleeve 38 provides support for a semi-rigid shim 50 that extends between the distal portion 16 and shim anchor sleeve 38. Shim 50 can be flat or oval and defines a radial plane out (not shown) of which shim 50 can be deflected upon the application of lateral deforming force. Upon release of the lateral deforming force, shim 50 will return with spring-like action back into its originally defined plane. A tang 52 anchors shim 50, such as by soldering, to distal portion 16. The purpose of the shim anchor sleeve 38 is to allow free movement of center tube 46 within the outer jacket portions 42 and 44, to support and position center tube 46, as well as to serve as an anchor point for shim 50 and a guide 55 for a pull cable 54.

Proximal outer jacket portion 42 houses and/or covers the portions of center tube 46 (inner catheter 12) adjacent to central torquing portion 18. While distal outer jacket portion 44 houses/covers various components coupled to or adjacent distal portion 16 of inner catheter body 12'. Shim anchor sleeve 38 is proximal to junction 40, and in a preferred embodiment the entire shim anchor sleeve 38 is bonded to the inside wall within the proximal outer jacket portion 42 adjacent to junction 40 with the distal outer jacket portion 44. It will be understood that the precise length and point of connection between shim anchor sleeve 38 and the outer jackets is selectable as desired, but that the design must not interfere with or otherwise impair normal operation of junction 40.

Pull cable 54 extends from the distal portion 16 of inner catheter body 12' where it is fixedly attached through a pull cable guide 55 or other retaining aperture in shim anchor sleeve 38. Pull cable guide 55 is positioned axially opposite shim 50, deflects distal portion 16 of inner catheter body 12' and bends shim 50. Pull cable 54 passes through pull cable guide 55 and extends to handpiece 20. At handpiece 20 pull cable 54 can be controllably pulled and released by a deflection knob (described herein) to cause selective deformation of distal portion 16 of inner catheter body 12'.

A spring 56 can be positioned in a surrounding/wrapped relationship around at least portions of center tube 46. In various embodiments, spring 56 can be a helical coil spring 56 fabricated using methods and materials well known in the art such as spring steels. Helical coil spring 56 imparts additional sidewall strength to the tubing material of center tube 46. Proper selection of the stiffness and number and placement of individual coils of helical coil spring 56 determines the bend radius of distal portion 16 of inner catheter body 12'. Furthermore, by using super elastic or shape memory materials of construction discussed below, distal portion 16 can be given predetermined curvature or shape.

In an additional preferred embodiment, center tube 46, shim 50, proximal and distal outer jacket portions 42 and 44 and/or the helical coil spring 56 are preferably made at least partially of, or otherwise comprise, a super elastic material such as nickel titanium alloys which can be given a selected shape. Other suitable materials include platinum, spring steel, stainless steel, shape memory or super elastic/shape memory alloys. This permits distal portion 16 of inner catheter body 12' to be temporarily deformed or otherwise curved for travel through the vasculature, inside the left ventricle or other body opening, and against a heart wall.

In the case of shape memory materials, a "memory" for a preformed shape can be temperature set distal portion 16 of inner catheter body 12'. When inner catheter 12 is in position, memory recall of the original preformed shape can be produced by any of a number of different ways. These include heating using electrically resistive material, electrically sensitive material, radio frequencies, circulating heated fluid and the like.

Figure 8:
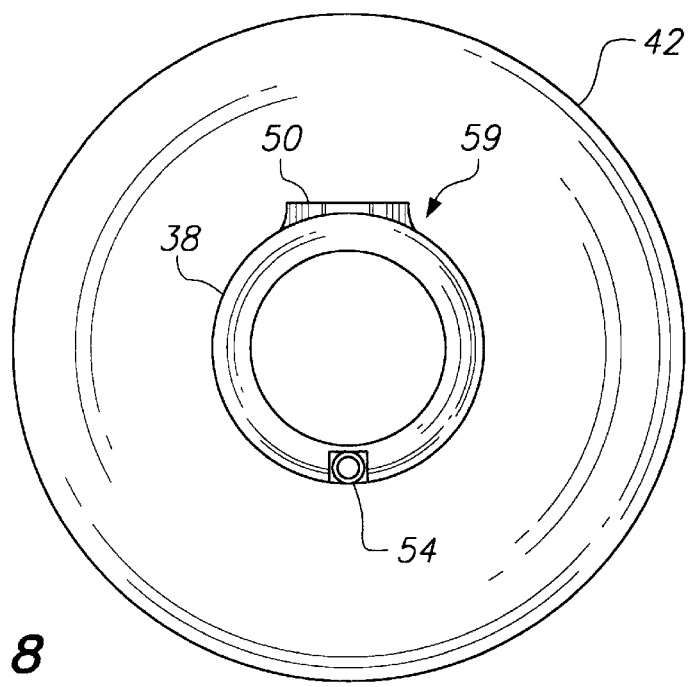
FIG. 8 is a representative end view of a preferred embodiment of the shim anchor sleeve used with the catheter system of FIG. 1.

FIG. 8 is a representative end view of a preferred embodiment of shim anchor sleeve 38. Shim 50 is linked to shim anchor sleeve 38 at a shim attachment point 59, radially opposite or otherwise operatively spaced relative to pull cable guide 55.

Figure 9:
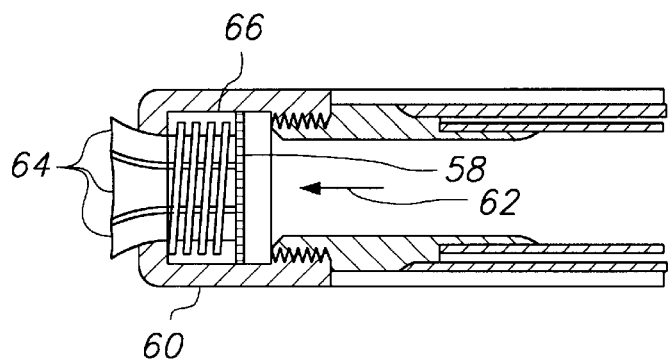
FIG. 9 illustrates an embodiment for anchoring the distal portion of the catheter system of FIG. 1.

Referring now to FIG. 9, a pressure plate 58 can be included and retained by a threadable end cap 60 threaded onto or otherwise coupled to distal portion 16 of inner catheter body 12'. When a force is applied to pressure plate 58 in direction 62, anchoring teeth 64 are extended as shown. When the force is released a biasing spring 66 repositions pressure plate 58 and retracts anchoring teeth 64.

As illustrated in FIGS. 8 and 9, helical coil biasing spring 66 and pressure plate 58 are retained and disposed adjacent to distal portion 16 of inner catheter body 12' end cap 60. In one embodiment, as pressure plate 58 is moved in direction 62, as by internal pressure or force created by fluid, rods or other biasing means, introducer 22 is extended. In various embodiments, introducer 22 can be advanced by applying pressure to pressure plate 58 (using flushing fluids or other means) through center tube 46. Additionally, introducer 22 can be attached to a pull tube which extends to handpiece 20 for control at the proximal end using a pull mechanism (not shown) known in the art. In this embodiment, pressure plate 58 may be omitted and helical biasing spring 66 is useful but optional.

Initially prior to positioning introducer 22 at the desired site in the heart, all or a portion of introducer 22 (including distal end 26) can be maintained in a retracted position within the center tube 46/outer catheter 11. Once the distal end of center tube 46 has been positioned at the desired site, introducer 22 is advanced distally out of center tube 46 using means described herein (e.g. a pull tube attached to a pull mechanism on handpiece 20). After completion of the procedure, distal introducer end 26 is then withdrawn back into center tube 46/outer catheter 12. Sensor 33' described herein, can be used to determine the amount that introducer 22 is advanced out of center tube 46.

Turning now to a discussion of the embodiments of the method(s) of delivering thermal energy to the heart including the endocardium, myocardium and epicardium, possible methods include, but are not limited to: i) positioning introducer 22 on or in endocardial, myocardial or epicardial tissue and then heating the desired tissue to a temperature described herein to create blood conducting pathways including revascularization channels, blood conducting pockets/zones or angiogenesis sites ii) heating introducer 22 to a temperature described herein and then positioning introducer 22 on or in endocardial, myocardial or epicardial tissue and then heating the desired tissue to a temperature described herein to create blood conducting pathways including revascularization channels, blood conducting pockets or zones or angiogenesis sites. These embodiments can apply to percutaneous/vascular, minimally invasive surgical or open chest surgical procedures discussed herein.

Figure 10:
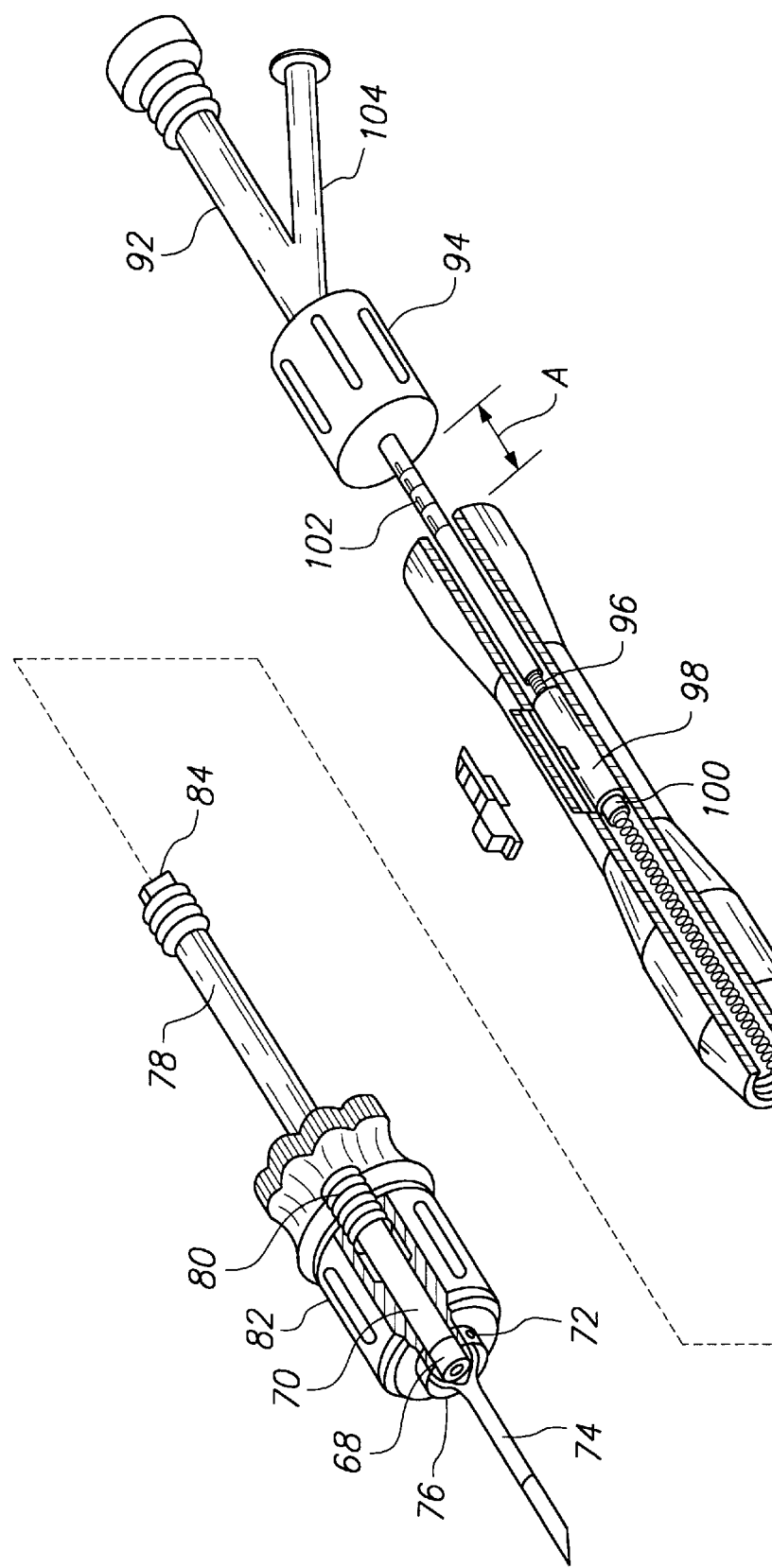
FIG. 10 is a partially cut-away and partially exploded representative view of the handpiece of FIG. 1 with a deflection component.
Figure 11:
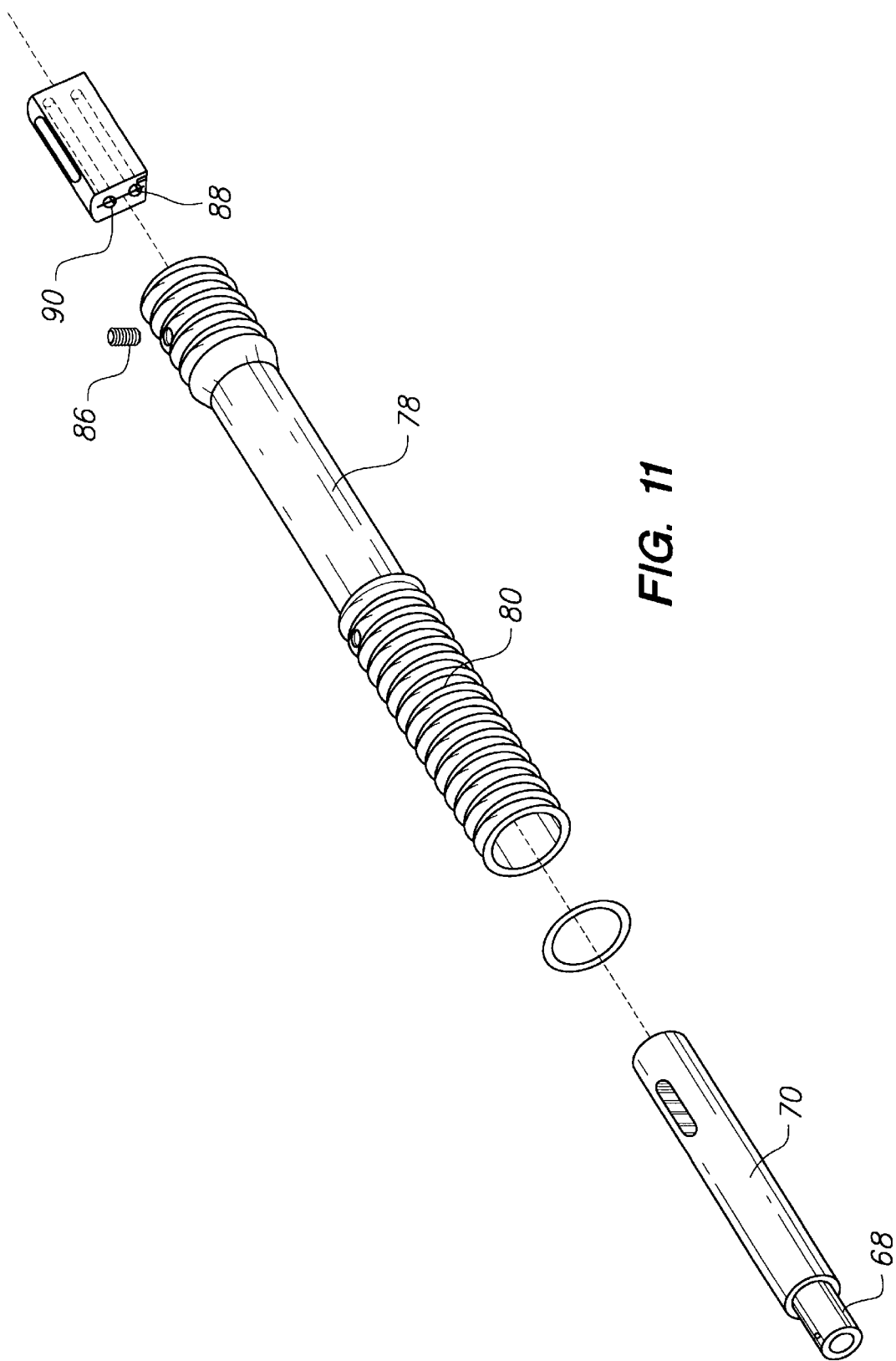
FIG. 11 is a representative exploded view of the internal assembly of a deflection component of the catheter system of FIG. 1.
Figure 12:
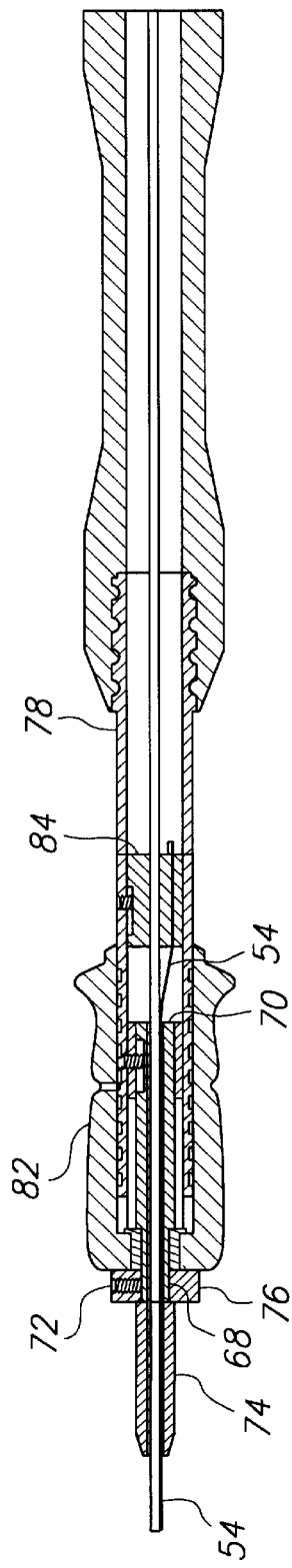
FIG. 12 is another drawing illustrating the deflection means of FIG. 11.

Referring now to FIGS. 10 through 12, proximal outer jacket portion 42 (as shown in previous figures) terminates at its proximal end and is coupled to a distal, inside stepped portion 68 of catheter base 70 by setscrew 72, or by other means including adhesive, etc. An optional strain relief 74 is fastened to either or both proximal catheter jacket portion 42 or to the distal, stepped portion 68 and/or the catheter base 70, or is otherwise coupled thereabouts, such as by setscrew 72. Strain relief 74 serves to minimize the effect of deflection or other handling of central torquing portion 18 and distal portion 16 of catheter body on handpiece 20. A retaining collar 76 is provided around the strain relief 74 and distal, stepped portion 68. A hollow, tubular deflection housing tube 78 houses catheter base 70 and has a first one or more external helical threaded portions 80 located at the distal end of the deflection housing tube 78. A deflection knob 82 has corresponding helical threads located on an inner, annular surface. Deflection knob 82 is threadably coupled to threaded portion 80 at the distal end of deflection housing tube 78. Thus, deflection knob 82 is able to rotate on threaded portion 80 above catheter base 70, retained in place by retaining collar 76 and maintains the axial position of the catheter base 70 relative to deflection knob 82.

Pull cable 54 extends from distal portion 16 of inner catheter body 12' past catheter base 70, through deflection housing tube 78 and terminates at pull cable stop 84. Pull cable stop 84 is fixed into position relative to deflection housing tube 78 by a setscrew 86. A slot formed in pull cable stop 84 permits attachment of setscrew 86 in several locations and enables adjustment of the tension of pull cable 54 to effect the overall sensitivity of the deflection assembly. As shown in FIGS. 11 and 12, pull cable 54 may pass through pull cable stop 84 through aperture 88 to be retained thereby, or will terminate at pull cable stop 84 by bonding or other means. Furthermore, center tube 46 passes through pull cable stop 84 through aperture 90 as shown, or pull cable stop 84 can be positioned to one side of the proximal end of deflection housing tube 78 (not shown) for lateral clearance of center tube 46 therethrough. As deflection knob 82 is rotated in one direction towards the distal end of deflection housing tube 78, the distance between the axial position of the deflection knob 82 and the proximal end of the deflection housing tube 78 is increased, resulting in increased tension in the pull cable 54, deflection of the flat shim 50 out of its own plane, and advancement of the proximal outer jacket portion 42 relative to the pull cable 54. As deflection knob 82 is rotated in the opposite direction, the distance between the axial position of deflection knob 82 and deflection housing tube 78 is decreased, thereby resulting in a corresponding decrease in tension of the pull cable 54 and a return to an un-deflected position.

Referring now to FIG. 10, an adaptor 92 (also called advancement member 92) can be coupled to catheter base 70 (coupled to inner catheter body 12') and/or deflection knob 82. In various embodiments adapter 92 can be a "Toughy-Borst" type compression adaptor 92 including two arm or three arm type adaptors known in the art. A depth-stop control nut 94, or other manually or otherwise controllable depth stop means, can be provided distal to adapter 92. An extension 96 extends to advance a slider 98 with a fluid seal 100. Center tube 46 floats freely through catheter base 70, deflection housing tube 78 and through fluid seal 100, and terminates within extension. Depth stop control nut 94 can be positioned as desired on extension 96 so as to limit extension of introducer 22. Thus, as control nut 94 is moved along extension 96, a maximum distance A can be traveled in precise increments, optionally by use of a calibrated depth scale 102 threaded over extension 96 and/or extending from control nut 94.

A saline flush, drug solution, visualization or other therapeutic agent containing fluid can be provided to inner catheter 12 or outer catheter 11 via a branched arm 104 of adaptor 92. Saline solution, medication or other such fluid fills adapter 92. Proximal fluid seal such as compression nut 94, or other sealing means, creates a seal. Suitable sealing means include rubber o-rings, as shown, rubber diaphragms, other elastic members and the like. Fluid seal 100 and/or compression nut 94 serves to prevent saline or other fluid from escaping past adapter 92.

Furthermore, the back flow of blood from the left ventricle into inner catheter 12 can be prevented by maintaining the pressure of the fluid in inner catheter 12 or outer catheter 11 somewhat above left ventricle pressures (typically 120 mm. Hg or greater). Additionally, fluid seal 100, as described in the foregoing, prevents fluid flow or back flush around the proximal end center tube 46.

Figure 13:
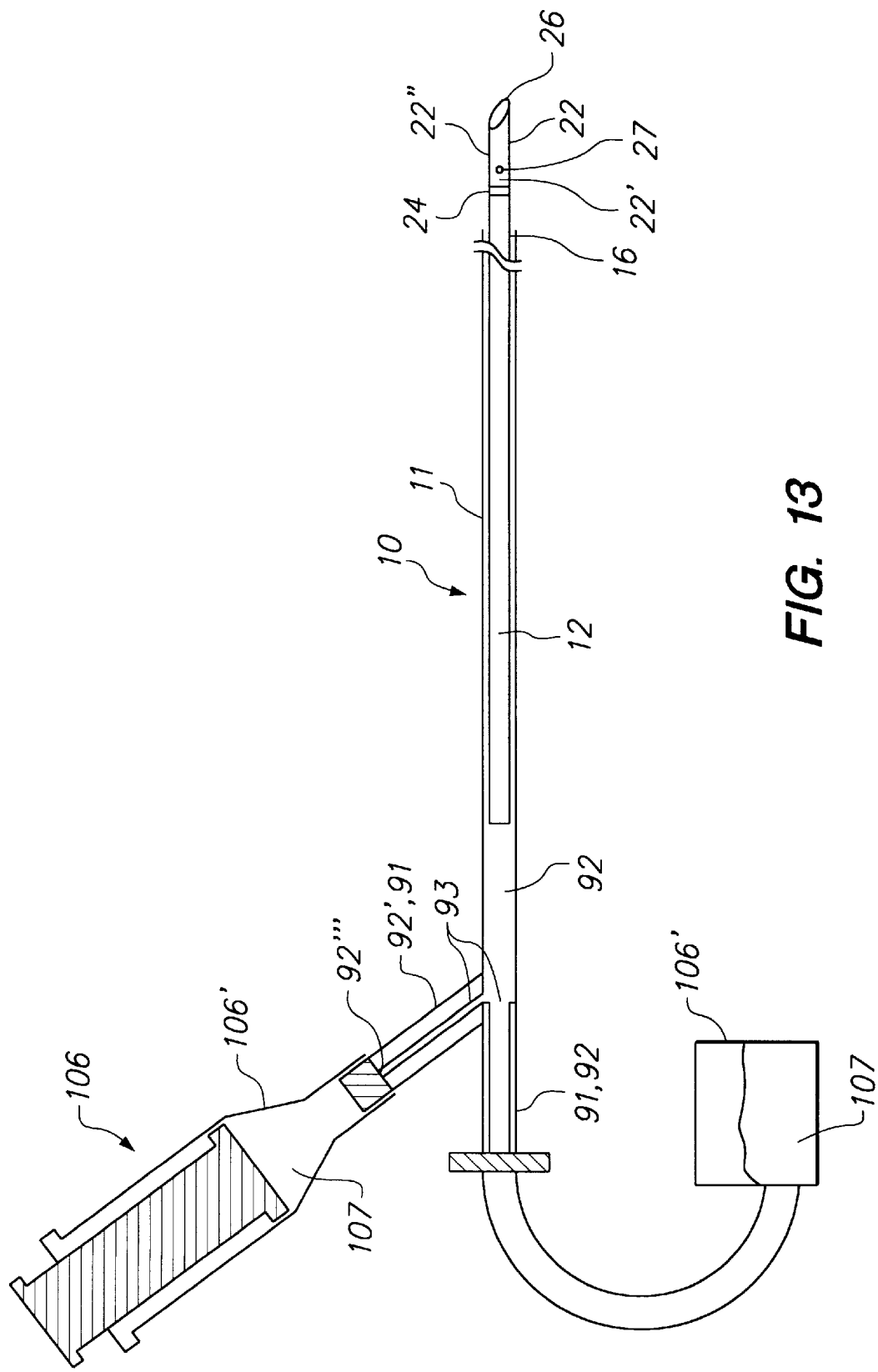
FIG. 13 is a representative isometric view of a drug delivery apparatus coupled to the proximal end of the handpiece.

FIG. 13 is a representative isometric view of a drug delivery or dispensing apparatus 106 fluidically coupled to outer catheter body 11' through use of adaptor 92. Adaptor 92 has one or more lumens 93 and may have one or more adaptor arms 91 which may be angled 92' or straight 92". Drug delivery apparatus 106 may be coupled to either adaptor arms 92' or 92" via a tubular connector 92'" that is configured to be coupled to medical tubing /tubular connectors well known in the art such as the Luer type. Arms 92' and 92" may also provide ports/access sites for the manipulation or advancement of inner catheter 12 and introducer 22. Other medical devices and instrumentation (e.g. aspiration devices, fiber optic viewing devices and pressure/flow measurement instrumentation, etc) may be coupled to inner catheter 12, outer catheter 11, or handpiece 20 via either arm 92' or 92". One or more medicaments 107 can be disposed in or otherwise coupled to drug delivery apparatus 106 or in a medicament reservoir 106' which may be coupled to drug delivery apparatus 106. Drug delivery apparatus 106 can be manually or automatically activated, adjustable or programmable to dispense individual aliquots of medicament 107, or a predetermined volume at a predetermined or specified rate as desired. In various embodiments, medicament 107 can include therapeutic agents, such as beta blockers, nitrates and calcium channel blockers, b-agonists and digitalis; and diagnostic agents such as contrast media (both fluoroscopic and echogenic) and diagnostic antibody-based compounds known in the art. Also, in various embodiments, medicament 107 can be dispensed through the distal end 26 of introducer 22 or through one or more apertures 27 in the wall 22' of introducer 22 or any point along its longitudinal length 22". In further embodiments, medicament 107 can be dispensed through an inner catheter lumen 15, a separate outer catheter lumen 11'" (not occupied by inner catheter 12) or via a third catheter (not shown) positioned in outer catheter 11.

Figure 14:
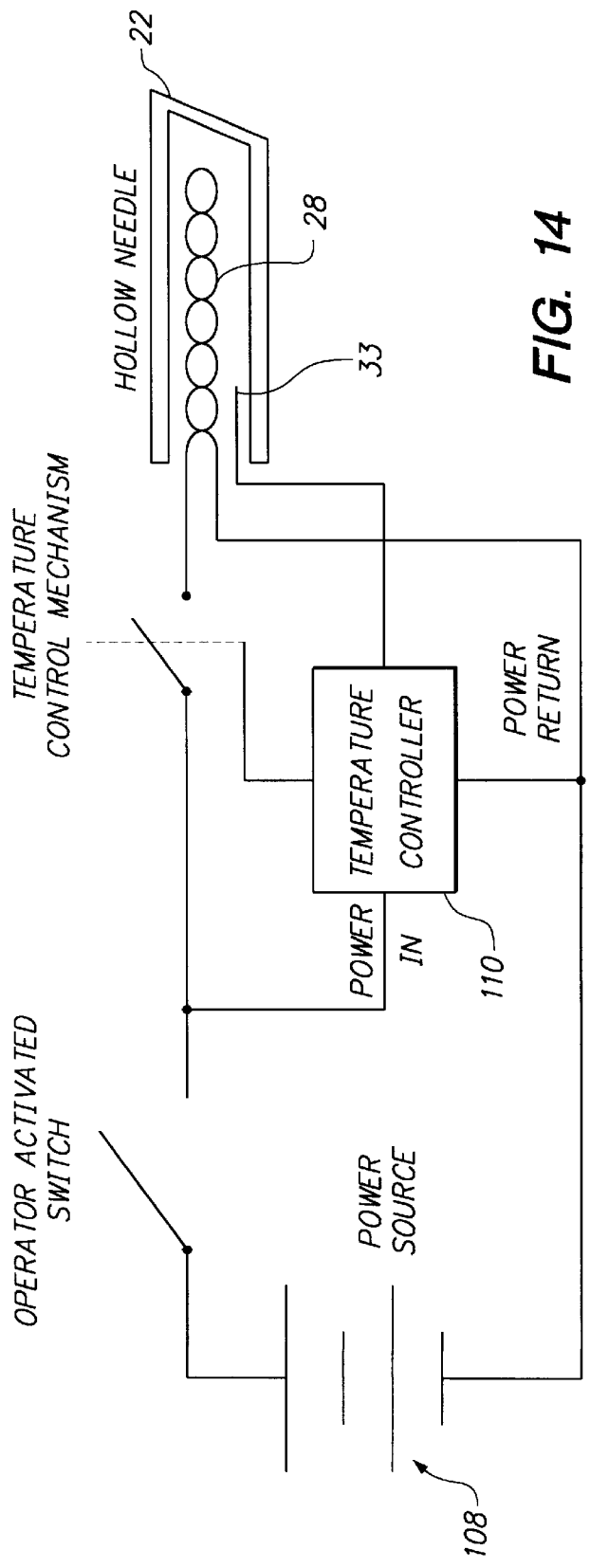
FIG. 14 is a schematic diagram of the power source with a temperature controller.

Referring now to FIG. 14, a power source 108 provides current to resistive heater element 28. Power source 108 can be an AC or DC source configured for medical operating room applications and safety standards including, but not limited to, a battery (e.g. lead acid). Power source 108 may include one or more of the following features to prevent ground-fault and other micro shock hazards: i) isolated transformer, ii) one or more optically isolated circuits, iii) ground-fault circuit interrupters, iv) current limiter placed in series with patient leads, and iv) use of double insulation. When actuated, power source 108 delivers power to a temperature controller 110. Temperature controller 110 monitors the temperature of resistive heater element 28 and/or introducer 22 as measured by thermal sensor 33. If the temperature measured is below a set point, additional power is delivered to resistive heater element 28. When the measured temperature exceeds the set point, current to resistive heater element 28 is reduced in an appropriate amount as determined by a control algorithm (e.g. a proportional integral derivative algorithm) electronically stored in the circuitry of controller 110. This can be achieved with an on/off switch or a linear current driver. The inclusion of thermal sensor 33 and temperature controller 110 are optional and inner catheter 12 can be operated with a fixed current that is delivered for a selected period of time. Additionally, an internal timer may be included to start and stop current flow to resistive heater element 28. Current and time parameters can be selected to provide a desired temperature profile. In one embodiment temperature controller 110 controls the temperature of introducer 22 in the range 50 to 120° C. with specific embodiments of 70, 80, 90, 100 and 110° C.

In one embodiment, controller 110 can be electronically coupled to contact sensor 33' in order to control the delivery of power to introducer 22. In this embodiment, controller 110 can be configured to prevent the delivery of power and subsequent heating of introducer 22 until one or more of the following events occurs: i) the distal end 26 of introducer 22 contacts endocardial, myocardial or epicardial tissue or ii) the entire conductive region of introducer 22 is inserted in endocardial, myocardial or epicardial tissue.

Figure 15:
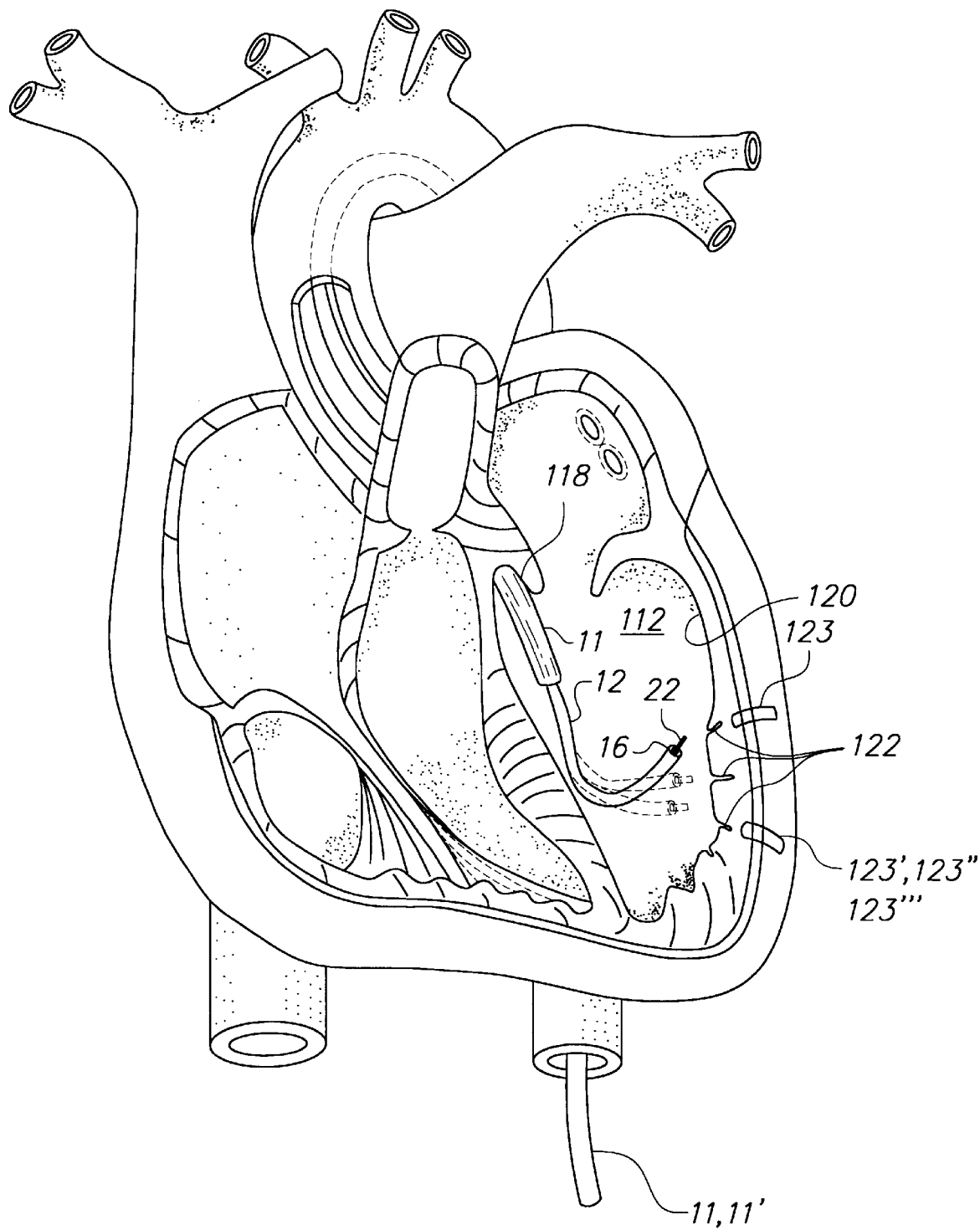
FIG. 15 is a representative perspective view of a portion of the catheter system shown in FIG. 1 positioned in the left ventricle.

FIG. 15 is a representative perspective view of the outer catheter 11 and inner catheter 12 within the left ventricle 112. As indicated above with regard to FIGS. 1 through 14, catheter system 10 (including outer catheter 11 and inner catheter 12) is directed through the vasculature into the left ventricle without the use of a traditional guiding catheter to achieve a stand alone catheter system 10. Guiding catheters are well known in the art and may be used with catheter system 10 including inner catheter 12 and/or outer catheter 11. Typically, entry into the vasculature is made through the femoral artery; however, a brachial approach may also be used. Prior to positioning of a guiding catheter (not shown) into the heart, the physician may first position an optional guide wire (not shown) into the left ventricle 112. Then the physician slides guiding catheter over the guide wire, over the aortic arch 116 and subsequently, across the aortic valve 118 and into the left ventricle 112. Subsequently, the guide wire is then withdrawn and catheters 12 and/or 11 are advanced through guiding catheter 114. However when catheter system 10 is configured as a stand alone catheter system, the traditional guide wire or guiding catheter need not be used. In the this case the guide wire is first positioned in the left ventricle 112. Catheter system 10 (including outer catheter 11 and/or inner catheter 12) is then advanced over the guide wire, over the aortic arch 116 and subsequently, across the aortic valve 118 and into the left ventricle 112. This can be facilitated by the use of deflection device 21 or the advancement mechanism described herein. Outer catheter 11 can then be guided into a selected position adjacent a selected surface 120, in this case a portion of endocardium (for surgical methods this surface may the epicardium).

Subsequently, inner catheter 12 is then advanced through outer catheter 11 to position introducer 22 on or in the selected surface 120 with subsequent energy delivery to a treatment point 122 in the endocardium, myocardium or epicardium. Thermal energy delivery (or other form of energy treatment) at treatment points 122 results in the formation of blood conducting pathways 123 which can be revascularization channels 123', blood conducting pockets/zones 123" and/or angiogenesis stimulation sites 123'''. The placement of introducer 22, including distal portion 26, at a selected surface and subsequent advancement into the heart wall to a treatment point 122 can be facilitated by the use of deflection device 21 and or a deflection mechanism described herein. Using deflection device 21 alone or in combination with the advancement mechanism, inner catheter 12 can be manipulated (e.g. deflected, twisted, or advanced; alone or in combination) to advance introducer 22 through the endocardium into the myocardium or epicardium, deliver thermal energy to the selected myocardial or epicardial tissue site with minimal repositioning of catheters 11 and 12, or without having to use a visualization or diagnostic modality (e.g. fluoroscopy), and removing introducer 22 from the heart. Using this approach, inner catheter 12 can be used to treat a series of individual, selected treatment points 122 of the endocardium, myocardium, and epicardium without having to remove inner or outer catheter 12 and 11, resulting in both reduced procedure time and complication rates typically associated with cardiac catheterization or interventional procedures.

Furthermore, adjunct use of appropriate drug delivery apparatuses such as an infusion pump; blood seal means; depth stop apparatuses, such as clamps, bushings, etc.; visualization means, such as a fiber optic view scope; marker means as well as other hardware and methodology, can be implemented singularly or in combination with catheter system 10. In various embodiments, angiogenesis stimulation agents can be delivered to the heart through lumen 15 in inner catheter 12 or lumen 11''' in outer catheter 11.

It will further be understood that while the present invention has been described for the introduction of introducer 22 through endocardial surfaces in the left ventricle, the apparatus and methods described herein are equally intended for use in any suitable medical procedure, including, but not limited to, diagnostic and interventional procedures, where any device need be inserted and/or advanced through a guiding catheter to an opening or other point within the body in order to perform other medical procedures including laser treatment, drug delivery, visualization, biopsy and the like. Angiogenesis stimulation can be performed by using thermal energy (in the form of resistive heating, laser energy or both) to create thermally treated stimulation zones or pockets, optionally interconnected (at least initially) by small channels through the tissue, for the introduction of blood born growth and healing factors, along with stimulated capillary growth surrounding the thermally treated zones. Such stimulation zones allow increased blood flow to previously ischemic and/or nonfunctional cardiac tissue with a concomitant increased supply of oxygen and nutrients ultimately resulting in a revitalization of the treated sections of heart muscle.

In addition to the apparatus and methods described herein that utilize a percutaneous/vascular approach for delivering thermal energy to stimulate angiogenesis, alternative embodiments of the invention comprise apparatus and methods for delivering energy using surgical and minimally invasive surgical methods. Such embodiments allow the physician to access the heart through a sternotomy or through surgical access devices such as trocars or ports (described herein) positioned in smaller surgical incisions into the chest wall made between the ribs.

Figure 16:
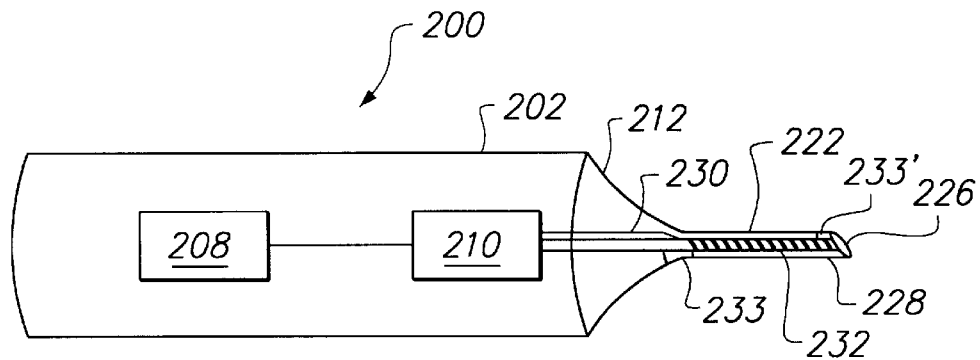
FIG. 16 is a perspective view of the minimally invasive surgical system.

One embodiment of a heart treatment apparatus 200 adapted for delivering energy via open chest cardiovascular surgical procedures and/or minimally invasive cardiovascular surgical procedures is depicted in FIG. 16. Apparatus 200 comprises a handpiece 202 having a distal end 212 as well as one, more or all of the components from the previously described embodiments including power source 208, electronic control circuitry 210, and an introducer 222 coupled to distal end 212. Likewise, introducer 222 has an energy delivery device 228 (which can be a resistive heating coil or other device described herein) electrically coupled to a conductive wire 230, in turn, electrically coupled to control system 210 (also called a controller 210). Introducer 222 may also have a thermal sensor 233 and a contact sensor 233', one or both of which may be coupled to controller 210. Distal end 212 may be elongated, tapered or otherwise shaped in order to facilitate access to desired epicardial and myocardial sites on or within the heart via a surgical incision in the chest, and/or through surgical access devices such as trocars and surgical ports known in the art. One suitable surgical access device is the Port-Access™ system manufactured by the Heartport Corporation, Redwood City, Calif.

Figure 17A:
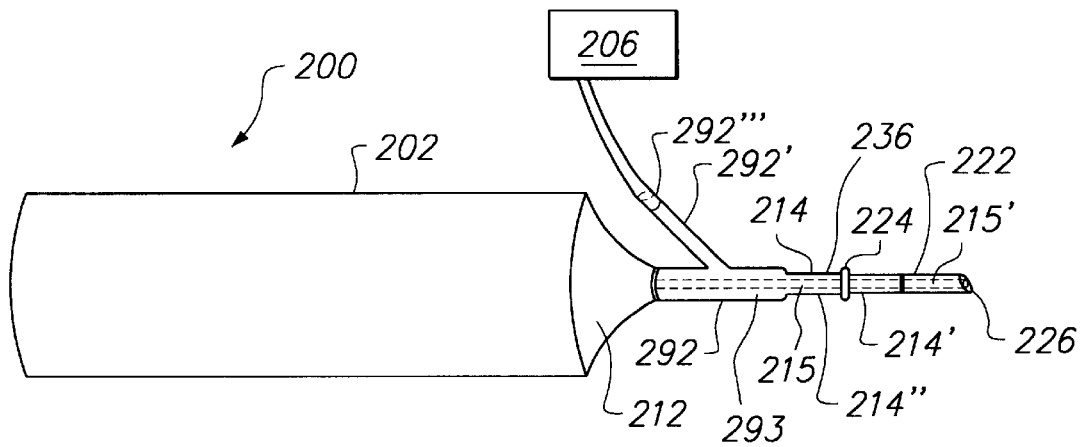
FIGS. 17A and 17B are perspective views of the minimally invasive surgical system with an elongated member.

In an alternative embodiment shown in FIG. 17A, apparatus 200 further comprises an elongated flexible member 214 that is coupled to handpiece distal end 212 and introducer 22. Elongated member 214 may have one or more lumens 215 and be made from any number of flexible polymers known in the art including, but not limited to, polyethylene, Pebax® or polyethylene terephthalate (PET) and in one embodiment may be a catheter that may have identical construction and components as inner catheter 12. Elongated member 214 has sufficient length and mechanical properties known in the art (including, but not limited to, pushability, torque ability, etc.) to allow the surgeon to position introducer 222 at desired epicardial and myocardial sites within the interior of the heart via a surgical incision in the chest, and/or through surgical access devices described herein. Elongated member 214 may also contain an adaptor 292 that has one or more arms 292' with lumens 293 that provide access to lumens 215. Various devices including drug delivery, irrigation and aspiration devices 206 can be fluidically coupled to apparatus 200 and elongated member 214 via connection to arms 292' using tubular connectors 292''', which are configured to be coupled to tubular connectors such as a Luer type connector, well known in the art. Specifically, air and fluid pathways can be established between these devices and lumens 215 via lumens 293. Elongated member 214 may also be deflectable using mechanisms described herein. In a related alternative embodiment, apparatus 200 can be a heart treatment system 200 comprising an inner elongated member 214' or inner catheter 214' (with one or more lumens 215') coupled to introducer 22 and disposed in an outer elongated member 214" coupled to the distal handpiece end 212. Similar to catheter system 10, inner elongated member 214' is configured to be axially advanceable in outer elongated member 214". Also, either inner catheter 214' or outer elongated member 214" may be fluidically coupled to adaptor 292. A sheath layer 236 may positioned in all or a portion of outer elongated member 214" to protect outer elongated member 214" from puncture by introducer 222 (including distal end 226) during axial advancement of inner catheter 214' through outer elongated member 214". In most other respects, heart treatment system 200 is similar to the embodiments of heart treatment apparatus 200 with elongated member 214 described above.

Figure 17B:
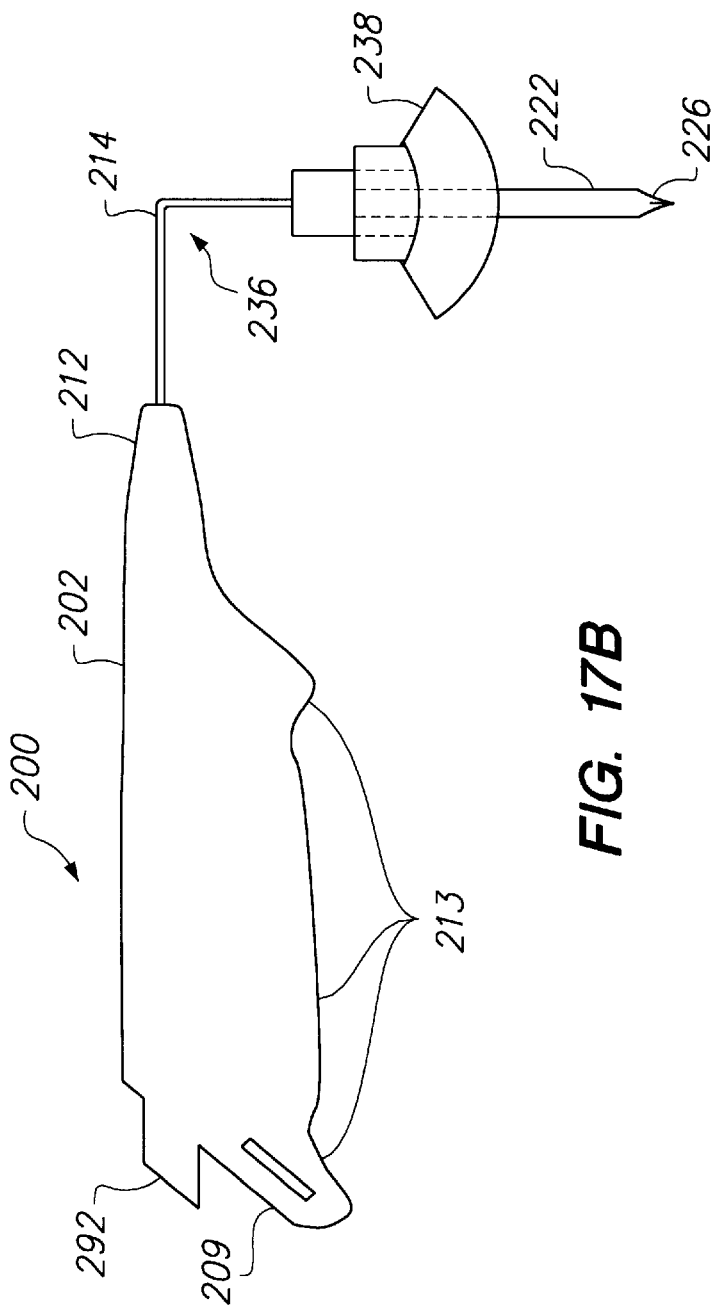

Referring now to FIG. 17B, in yet another alternative embodiment, handpiece 202 has a shape shown in the figure which includes a proximal end 209, a handgrip 213 and proximal adaptor 292 coupled to proximal end 209. Additionally, in this embodiment, elongated member 214 is bent at an angle 236, which may be in the range from 0 to 180° to facilitate positioning of introducer 222 at the desired epicardial and myocardial sites. Angle 236 may be pre-shaped or formed by the physician. Also, a positioning fixture 238 is coupled to the distal portion 216 of elongated member 214. Positioning fixture 238 functions to stabilize and/or minimize the movement of introducer 222 in the body. Additionally, positioning fixture 238 can serve to control or limit the depth of penetration of introducer 222 and introducer distal end 226 into coronary tissue including the myocardium, endocardium and surrounding vasculature. In various embodiments positioning fixture 238 can be positioned on the outside of the chest wall, at or near the surgical incision site, or on the surface of the heart or pericardium. In one embodiment positioning fixture 238 comprises a suction cup device well known in the art which can be temporarily adhered to the outside chest wall or the outside surface of the heart.

Figure 18A:
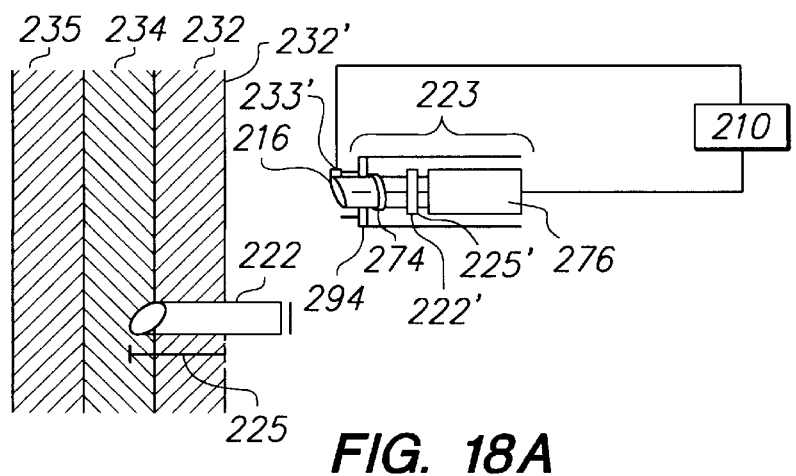
FIGS. 18A and 18B are cross sectional views illustrating the use of an advancing mechanism for the introducer.
Figure 18B:
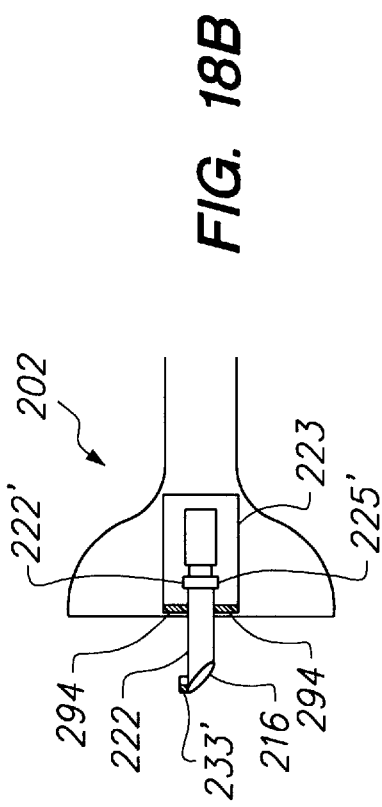

In another embodiment shown in FIGS. 18A and 18B, handpiece 202 is configured to controllably pierce an epicardial surface 232' of the heart and advance introducer 222 into the epicardium 232, myocardium 234 or endocardium 235. Such a handpiece is available under the name Sologrip™ from Eclipse Surgical Technologies, Sunnyvale, Calif. Piercing the heart from the epicardial surface is beneficial in performing TMR in terms of reducing acute bleeding, anchoring the device to the beating heart, and in reducing adhesions between the epicardium and the pericardium that may develop as a result of the procedure.

FIG. 18A is a cross sectional view of an electrically controllable advancement mechanism 223. The controllable advancement mechanism 223 includes introducer 222, an introducer flange 222' mechanically attached to introducer 222, a spring 274, a solenoid 276 and depth stop 294. Introducer 222 is driven by spring 274 as controlled electrically by solenoid 276, which can be coupled to controller 210 and/or a foot switch (not shown). This construction allows advancement mechanism 223 to be electronically controlled and also controls the depth of penetration 225 of introducer 222 into the heart. Specifically, the position of introducer flange 222' and depth stop 294 are configured to limit penetration distance 225. In various embodiments, the lateral position 225' of introducer flange 222' on introducer 222 is adjustable either manually (via use of a clamp or other mechanical means known in the art), or automatically using a servo mechanism well known in the art which may be coupled to controller 210. In one embodiment, control of advancement mechanism 223 can be facilitated by a contact sensor 233' positioned at or near introducer distal end 226 and coupled to controller 210. In this embodiment contact sensor 233' facilitates control of penetration depth 225 of introducer 222, by controlling the activation of solenoid 276 until contact is made between introducer distal end 226 and the epicardial surface. The time of the piercing of the heart can be set relative to the pace signal of the heart. Alternatively, the piercing can be timed so as to cause the heart to beat.

Referring now to FIGS. 19A, 19B and 19C, in various embodiments, catheter 310 (which can also be a catheter system 310 comprising an inner catheter 310' disposed in an outer catheter 310" analogous to catheters 12 and 11) may have a tip alignment mechanism 311 that serves to maintain the longitudinal alignment of introducer 322 with catheter body 312 (which can also be inner catheter body 312' or outer catheter body 312") before and during insertion of introducer 322 into endocardial or myocardial tissue. Tip alignment mechanism 311 comprises a differential screw mechanism 320 disposed within deflection knob 382. Mechanism 320 has a differential screw member 321, which in turn has two externally threaded sections 352 and 353, each with different pitches. Threaded section 353 causes tip deflection while threaded section 352 causes tip alignment compensation. Tip alignment may be achieved in part by movement of a catheter outer jacket 310''' (which also may be outer catheter 310") slidably positioned over catheter 310 and mechanically coupled to deflection knob 382. When deflection knob 382 is turned, a corresponding advancement or retraction of the catheter outer jacket 310''' and/or catheter 310 occurs, causing handle section 372 to move in relation to the proximal region of center or deflection housing tube 378, and the introducer thereby maintaining introducer alignment. FIGS. 19A, 19C and 19B show the sequential deflection of the distal tip section as the deflection knob 382 is turned. FIG. 19A shows the catheter distal portion 316 without advancement of introducer 22. FIG. 19B shows the catheter distal section deflected, and FIG. 19C shows the distal section deflected with advancement of introducer 322. Compression nut 394 acts as a seal component to prevent fluid within catheter 310 from being emitted from the handle while still allowing the translation of introducer 322. Introducer 322 is inserted into the catheter deflection housing tube 378, then introducer 322 and the catheter distal portion 316 are adjusted and aligned manually prior to use. As the distal catheter portion 316 is deflected as shown in FIG. 19B, differential screw 321 in knob 382 causes relative motion of the catheter body 312 and handle 372, thereby maintaining alignment between the catheter distal portion 316 and introducer distal section 326 using an improved auto-alignment knob incorporated into handle 372. FIG. 19C shows the distal portion 316 of the catheter deflected with the introducer 322 advanced using a ring-type knob 375 that surrounds the handle section 372 and facilitates introducer advancement to a preset depth according to a depth control knob 380.

Figure 20A:
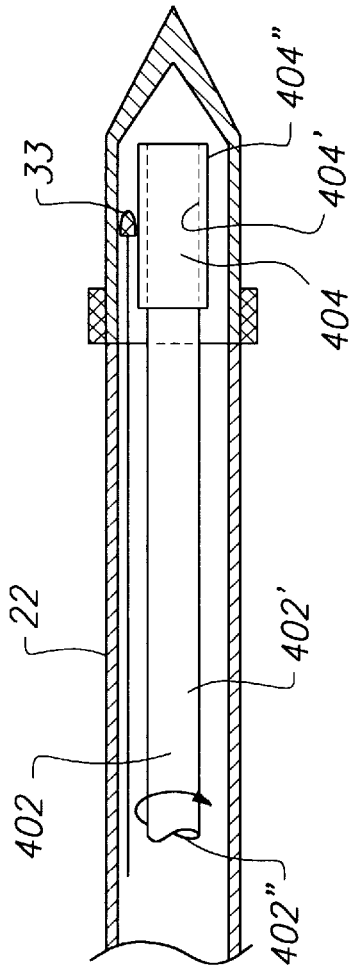
FIGS. 20A and 20B are cross sectional views illustrating the use of a rotating shaft and bearing used to heat the introducer by mechanical friction.
Figure 20B:
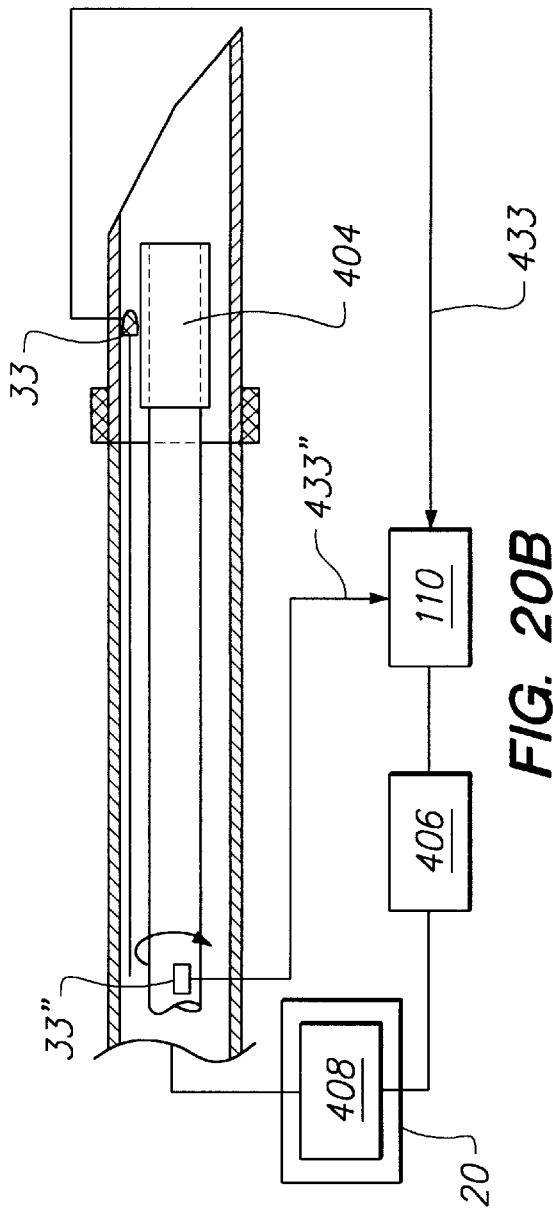

In another embodiment illustrated in FIGS. 20A and 20B, introducer 22 can be heated by friction between a rotating shaft 402 disposed inside inner catheter body 12' and a cylindrical bearing 404 disposed inside introducer 22. The bearing 404 has an interior surface 404' which contacts the exterior surface 402' of shaft 402 and a bearing exterior surface 404" which is mechanically and thermally coupled to introducer 22. One or more thermal sensors 33 may be positioned on the bearing 404 interior or exterior surfaces 404' and 404", as well as introducer 22. Also, one or more velocity sensors 33" may positioned at various locations on shaft 402. The bearing 404 may be made out of materials that are thermally conductive, have a high hardness (with specific embodiment in the range of 50–1000 Brinell) and are wear and fatigue resistant. Suitable materials for bearing 404 include hardened tool steel, tungsten carbide alloys and cobalt alloys and the like, all well known in the art. Suitable materials for shaft 402 include 304V and other stainless steels. One or both of shaft exterior surface 402' and bearing interior surface 404' can be roughened to increase the amount of friction between the two surfaces. Shaft 402 has a proximal end 402", which can be mechanically coupled to an electric motor 406 using crimping, soldering or clamps to link shaft 402 to motor 406. In various embodiments, shaft 402 can rotate at a speed of 1–10,000 rpm, with specific embodiments of 2000, 4000, 6000 and 8000 rpm. Suitable electrical motors include high rpm miniature brushless DC motors, AC motors and other high speed motors known in the art. The motor 406 is also coupled to controller 110, which in turn, is electronically coupled to thermal sensors 33 and/or velocity sensors 33". Controller 110 uses temperature and shaft velocity input signals 433 and 433" from sensors 33 and 33" so as to increase or decrease the speed of shaft 402 in an appropriate amount to maintain the temperature of introducer 22 at a particular set point. Signals 433 and 433" may be inputted to controller 110 through an input device (not shown), such as an electronic keypad electronically coupled to controller 110, or via a microcomputer interfaced with controller 110 through a data interface port, such as a serial port. In various embodiments, controller 110 may comprise a microprocessor or ASIC (both with embedded control software) electronically coupled to or disposed within catheter system 10. Suitable microprocessors include, but are not limited to, the Pentium® series microprocessors available from the Intel® corporation. In one embodiment, controller 110 is disposed within handpiece 20. The keypad can be positioned in handpiece 20 or can be coupled to inner catheter 12 via a data interface port, such as a serial port. In various embodiments, controller 110 may employ a control algorithm known in the art, such as a proportional integral control method, to adjust the speed of shaft 402 in an appropriate amount to maintain a set point temperature of introducer 22. In various embodiments, motor 406 can be positioned in handpiece 20, or can be located outside of handpiece 20 and coupled either to a section of shaft 402 that extends outside of the handle or to a drive system 408 positioned in handpiece 20 and mechanically coupled to shaft 402.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method of improving blood circulation in a patient's heart, comprising:

providing a catheter system including an outer catheter with an outer catheter distal end and at least one outer catheter lumen and an inner catheter configured to be advancable in the outer catheter, the inner catheter having a proximal portion, a distal portion, at least one inner catheter lumen, an introducer coupled to a distal portion of the inner catheter and a resistive heater element positioned in the introducer, the introducer including a tissue piercing distal end;

introducing the catheter system into a patient's vasculature;

advancing the tissue piercing distal end of the introducer into an interior of the heart at a selected heart tissue site; and controllably delivering energy from the resistive heater element to the selected heart tissue site to create a blood conducting pathway in the patient's heart including a revascularization channel.

2. The method of claim 1, wherein the tissue piercing distal end pierces an endocardium.

3. The method of claim 1, wherein the tissue piercing distal end pierces an endocardium without creating the channel.

4. The method of claim 1, wherein energy is delivered from the resistive heater element to the selected heart tissue site after the tissue piercing distal end pierces an endocardium.

5. The method of claim 4, wherein the selected heart tissue site is in a myocardium.

6. The method of claim 4, wherein at least a portion of the selected heart tissue site is in an endocardium.

7. The method of claim 4, wherein at least a portion of the selected heart tissue site is in an epicardium.

8. The method of claim 4, wherein the revascularization channel has a length not greater than 10 mm.

9. The method of claim 4, wherein the resistive heater element heats the introducer to a temperature not exceeding 120° C.

10. The method of claim 4, wherein the resistive heater element heats the introducer to a temperature range of 50–120° C.

11. The method of claim 1, further comprising the step of delivering a medicament to the heart.

12. The method of claim 1, wherein the blood conducting pathway is a blood conducting pocket, a blood conducting zone or an angiogenesis site.

13. The method of claim 1, wherein the introducer includes a column strength member positioned in the introducer.

14. The method of claim 1, wherein the introducer is heated by the resistive heater element before the tissue piercing distal end of the introducer pierces an endocardium.

15. A method of improving blood circulation in a patient's heart, comprising:

providing a catheter system including an outer catheter with an outer catheter distal end and at least one outer catheter lumen and an inner catheter configured to be advancable in the outer catheter, the inner catheter having a proximal portion, a distal portion, at least one inner catheter lumen, an introducer coupled to a distal portion of the inner catheter and a resistive heater element positioned in the introducer, the introducer including a tissue piercing distal end;

introducing the catheter system into a patient's vasculature;

advancing the tissue piercing distal end of the introducer into an interior of the heart at a selected heart site; and controllably delivering energy from the resistive heater element to the selected heart tissue site to stimulate angiogenesis.

16. A method of improving blood circulation in a patient's heart, comprising:

providing a catheter with at least one lumen, a proximal portion, a distal portion, an introducer including a tissue piercing distal end coupled to the distal portion and a resistive heater element positioned at the introducer;

introducing the catheter through a vasculature;

introducing the tissue piercing distal end of the catheter into the heart; and controllably delivering energy from the resistive heater element to a selected heart tissue site to create a blood conducting pathway in the patient's heart including a revascularization channel.

17. The method of claim 16, wherein the tissue piercing distal end pierces an endocardium.

18. The method of claim 16, wherein the tissue piercing distal end pierces an endocardium without creating the channel.

19. The method of claim 16, wherein energy is delivered from the resistive heater element to the selected heart tissue site after the tissue piercing distal end pierces an endocardium.

20. The method of claim 19, wherein the selected heart tissue site is in a myocardium.

21. The method of claim 19, wherein at least a portion of the selected heart tissue site is in the endocardium.

22. The method of claim 19, wherein at least a portion of the selected heart tissue site is in the epicardium.

23. The method of claim 19, wherein the revascularization channel has a length not greater than 10 mm.

24. The method of claim 19, wherein the resistive heater element heats the introducer to a temperature not exceeding 120° C.

25. The method of claim 19, wherein the resistive heater element heats the introducer to a temperature range of 50–120° C.

26. The method of claim 16, further comprising delivering a medicament to the heart.

27. The method of claim 16, wherein the blood conducting pathway is a blood conducting pocket, a blood conducting zone or an angiogenesis site.

28. The method of claim 16, wherein the introducer includes a column strength member positioned in the introducer.

29. The method of claim 16, wherein the introducer is heated by the resistive heater element before the tissue piercing distal end of the introducer pierces an endocardium.

30. A method of improving blood circulation in a patient's heart, comprising:
providing a catheter with at least one lumen, a proximal portion, a distal portion, an introducer including a tissue piercing distal end coupled to the distal portion and a resistive heater element positioned at the introducer;
introducing the catheter through a vasculature;
introducing the tissue piercing distal end of the catheter into the heart; and
controllably delivering energy from the resistive heater element to a selected heart tissue site to stimulate angiogenesis.

31. A method of improving blood circulation in a patient's heart, comprising:
providing a heart treatment apparatus comprising:
a handpiece with a proximal end and a distal end;
an elongated member with a proximal portion and a distal portion, the elongated member defining at least one lumen, the elongated member proximal portion coupled to the handpiece distal end;
an introducer with a tissue piercing distal end, the introducer coupled to the distal portion of the elongated member; and
a resistive heater element positioned in the introducer;
advancing the tissue piercing distal end through an epicardial surface and into an interior of the heart; and
controllably delivering energy from the resistive heater element to a selected heart tissue site to create a blood conducting pathway in the patient's heart including a revascularization channel.

32. The method of claim 31, wherein the tissue piercing distal end is advanced a fixed penetration depth into the interior of the heart.

33. The method of claim 32, wherein the penetration depth is adjustable.

34. The method of claim 31, wherein the tissue piercing distal end pierces an epicardium.

35. The method of claim 31, wherein the tissue piercing distal end pierces an epicardium without creating the channel.

36. The method of claim 31, wherein energy is delivered from the resistive heater element to the selected heart tissue site after the tissue piercing distal end pierces an epicardium.

37. The method of claim 36, wherein the selected heart tissue site is in a myocardium.

38. The method of claim 36, wherein at least a portion of the selected heart tissue site is in an endocardium.

39. The method of claim 36, wherein at least a portion of the selected heart tissue site is in the epicardium.

40. The method of claim 36, wherein the revascularization channel has a length not greater than 10 mm.

41. The method of claim 36, wherein the resistive heater element heats the introducer to a temperature not exceeding 120° C.

42. The method of claim 36, wherein the resistive heater element heats the introducer to a temperature range of 50–120° C.

43. The method of claim 31, further comprising the step of delivering a medicament to the heart.

44. The method of claim 31, wherein the blood conducting pathway is a blood conducting pocket, a blood conducting zone or an angiogenesis site.

45. The method of claim 31, wherein the introducer includes a column strength member positioned in the introducer.

46. The method of claim 31, wherein the introducer is heated by the resistive heater element before the tissue piercing distal end of the introducer pierces an epicardium.

47. A method of improving blood circulation in a patient's heart, comprising:
providing a heart treatment apparatus comprising:
a handpiece with a proximal end and a distal end;
an elongated member with a proximal portion and a distal portion, the elongated member defining at least one lumen, the elongated member proximal portion coupled to the handpiece distal end;
an introducer with a tissue piercing distal end, the introducer coupled to the distal portion of the elongated member; and
a resistive heater element positioned in the introducer;
advancing the tissue piercing distal end through an epicardial surface and into an interior of the heart, and;
controllably delivering energy from the resistive heater element to a selected heart tissue site to stimulate angiogenesis.

48. A method of improving blood circulation in a patient's heart, comprising:
providing a heart treatment system comprising:
a handpiece with a proximal end and a distal end;
an outer elongated member with an outer elongated member proximal portion and an outer elongated member distal portion, the outer elongated member defining at least one outer elongated member lumen, the outer elongated member proximal portion coupled to the handpiece distal end;
an inner catheter configured to be advancable within the outer elongated member lumen, the inner catheter including a proximal portion and a distal portion, the inner catheter defining at least one inner catheter lumen;

an introducer coupled to the distal portion of the inner catheter, the introducer including a tissue piercing distal end; and a resistive heater element positioned in the introducer;

advancing the tissue piercing distal end through an epicardial surface and into an interior of the heart; and controllably delivering energy from the resistive heater element to a selected heart tissue site to create a blood conducting pathway in the patient's heart including a revascularization channel.

49. The method of claim 48, wherein the tissue piercing distal end is advanced a fixed penetration depth into the interior of the heart.

50. The method of claim 49, wherein the penetration depth is adjustable.

51. The method of claim 48, wherein the tissue piercing distal end pierces an epicardium.

52. The method of claim 48, wherein the tissue piercing distal end pierces an epicardium without creating the channel.

53. The method of claim 48, wherein energy is delivered from the resistive heater element to the selected heart tissue site after the tissue piercing distal end pierces an epicardium.

54. The method of claim 53, wherein the selected heart tissue site is in a myocardium.

55. The method of claim 53, wherein at least a portion of the selected heart tissue site is in an endocardium.

56. The method of claim 53, wherein at least a portion of the selected heart tissue site is in the epicardium.

57. The method of claim 53, wherein the revascularization channel has a length not greater than 10 mm.

58. The method of claim 53, wherein the resistive heater element heats the introducer to a temperature not exceeding 120° C.

59. The method of claim 53, wherein the resistive heater element heats the introducer to a temperature range of 50–120° C.

60. The method of claim 48, further comprising the step of delivering a medicament to the heart.

61. The method of claim 48, wherein the blood conducting pathway is a blood conducting pocket, a blood conducting zone or an angiogenesis site.

62. The method of claim 48, wherein the introducer includes a column strength member positioned in the introducer.

63. The method of claim 48, wherein the introducer is heated by the resistive heater element before the tissue piercing distal end of the introducer pierces an epicardium.

64. A method of improving blood circulation in a patient's heart, comprising:

providing a heart treatment system comprising:

a handpiece with a proximal end and a distal end;

an outer elongated member with an outer elongated member proximal portion and an outer elongated member distal portion, the outer elongated member defining at least one outer elongated member lumen, the outer elongated member proximal portion coupled to the handpiece distal end;

an inner catheter configured to be advanceable within the outer elongated member lumen, the inner catheter including a proximal portion and a distal portion, the inner catheter defining at least one inner catheter lumen;

an introducer coupled to the distal portion of the inner catheter, the introducer including a tissue piercing distal end; and a resistive heater element positioned in the introducer;

advancing the tissue piercing distal end through an epicardial surface and into an interior of the heart; and controllably delivering energy from the resistive heater element to a selected heart tissue site to stimulate angiogenesis.

* * * * *